United States Patent
Avery et al.

(10) Patent No.: US 8,962,628 B2
(45) Date of Patent: Feb. 24, 2015

(54) HERBICIDAL 5H-QUINOXALINE-6-ONE DERIVATIVES DETAILED DESCRIPTION

(75) Inventors: Alaric James Avery, Bracknell (GB); Alain De Mesmaeker, Stein (CH); Nicholas Phillip Mulholland, Bracknell (GB); Nigel James Willetts, Bracknell (GB); Paul Anthony Worthington, Maidenhead (GB)

(73) Assignee: Syngenta Limited, Guildford (GB)

( * ) Notice: Subject to any disclaimer, the term of this patent is extended or adjusted under 35 U.S.C. 154(b) by 0 days.

(21) Appl. No.: 13/884,671

(22) PCT Filed: Oct. 14, 2011

(86) PCT No.: PCT/EP2011/068037
§ 371 (c)(1),
(2), (4) Date: Jul. 23, 2013

(87) PCT Pub. No.: WO2012/062531
PCT Pub. Date: May 18, 2012

(65) Prior Publication Data
US 2013/0303370 A1    Nov. 14, 2013

(30) Foreign Application Priority Data
Nov. 12, 2010  (GB) .................................. 1019229.2
Nov. 15, 2010  (GB) .................................. 1019305.0

(51) Int. Cl.
*A61K 31/498*  (2006.01)
*C07D 241/40*  (2006.01)
*A01N 43/60*  (2006.01)
*C07D 241/12*  (2006.01)
*C07D 241/42*  (2006.01)
*C07D 491/04*  (2006.01)
*C07D 491/052*  (2006.01)

(52) U.S. Cl.
CPC .............. *A01N 43/60* (2013.01); *C07D 241/12* (2013.01); *C07D 241/42* (2013.01); *C07D 491/04* (2013.01); *C07D 491/052* (2013.01)
USPC .......................................... 514/249; 544/353

(58) Field of Classification Search
CPC ............................ A61K 31/498; C07D 241/40
USPC ........................................... 514/249; 544/353
See application file for complete search history.

(56) References Cited

FOREIGN PATENT DOCUMENTS

| WO | 2008/09908 | 1/2008 |
|----|-----------|--------|
| WO | 2010/130970 | 11/2010 |
| WO | 2010/139657 | 12/2010 |

OTHER PUBLICATIONS

International Search Report, International Application No. PCT/EP2011/068037, completion date: Dec. 8, 2011.

*Primary Examiner* — Douglas M Willis
(74) *Attorney, Agent, or Firm* — James Cueva

(57) ABSTRACT

The present invention provides a compound of formula (I) wherein $R^4$ is of sub-formula (a) or (b) and wherein the other substituents are as defined in the specification. The compounds of formula (I) are potentially useful as herbicides.

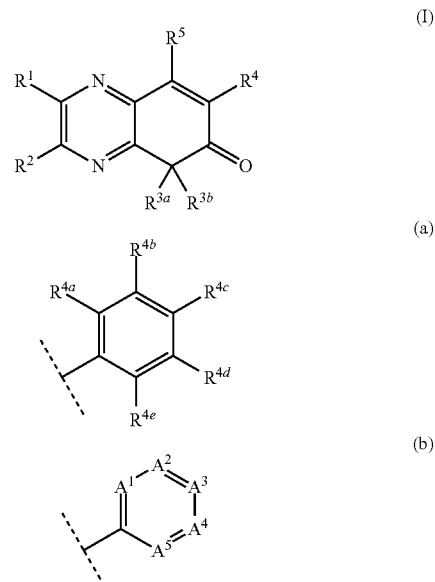

13 Claims, No Drawings

HERBICIDAL 5H-QUINOXALINE-6-ONE DERIVATIVES DETAILED DESCRIPTION

This application is a 371 of International Application No. PCT/EP2011/068037 filed Oct. 14, 2011, which claims priority to EP 1019229.2 filed Nov. 12, 2010, and EP 1019305.0 filed Nov. 15, 2010, the contents of which are incorporated herein by reference.

The present invention relates to 5H-quinoxaline-6-one derivatives, to processes and intermediates for making these compounds, to herbicidal compositions comprising these compounds, and to methods of using these compounds to control plant growth.

WO 2008/009908, WO 2008/071918 A1 and WO 2009/090402 (all Syngenta Limited) disclose herbicidal pyrido[2,3-b]pyrazine derivatives.

WO 2009/063180 (Syngenta Limited) discloses certain 1H-2-thia-1,5,8-triaza-naphthalene-2,2-dioxides derivatives with herbicidal and plant-growth-inhibiting properties.

WO2010/130970 (Syngenta Limited), filed on 6 May 2010 with a priority date of 14 May 2009, discloses certain 6,6-dioxo-6-thia-1,4-diaza-naphthalene derivatives having herbicidal properties.

US2011/105329 (BASF SE), discloses substituted quinolinones and their use as herbicides.

It has now surprisingly been found that certain 5H-quinoxaline-6-one derivatives have herbicidal and/or plant-growth-inhibiting properties.

The present invention therefore provides a compound of formula (I):

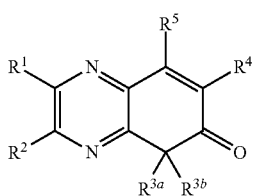

(I)

wherein: $R^1$ and $R^2$ are independently hydrogen, halogen, $C_1$-$C_4$alkyl, $C_1$-$C_2$fluoroalkyl, $C_1$-$C_2$alkoxy-$C_1$-$C_2$alkyl-, hydroxy, $C_1$-$C_4$alkoxy, $C_1$-$C_2$fluoroalkoxy, or $C_1$-$C_2$alkoxy-$CH_2CH_2O$—; $R^{3a}$ and $R^{3b}$ are independently halogen (e.g. fluorine or chlorine), $C_1$-$C_4$alkyl, $C_1$-$C_4$-fluoroalkyl, $C_1$-$C_4$-chloroalkyl, $C_1$-$C_2$alkoxy-$C_1$-$C_2$alkyl-, $C_2$-$C_4$alkenyl, $C_2$-$C_4$fluoroalkenyl, $C_2$-$C_4$-chloroalkenyl, $C_2$-$C_4$alkynyl, $C_2$-$C_4$-fluoroalkynyl, $C_2$-$C_4$chloroalkynyl, $C_3$-$C_6$cycloalkyl-$(CH_2)_m$— or $C_3$-$C_6$cycloalkyl-$(CH_2)_m$-substituted on the cycloalkyl ring by 1 or 2 methyl groups and wherein m is 0 or 1, $C_1$-$C_3$alkyl-carbonyl-, $C_3$alkoxy-carbonyl-, $C_1$-$C_2$chloroalkyl-carbonyl-, or $C_1$-$C_2$fluoroalkyl-carbonyl-; phenyl or phenyl substituted by one or two of independently fluorine and/or methyl; or heterocyclyl-methyl- in which the heterocyclyl is a 4-, 5-, or 6-membered saturated monocyclic heterocyclic ring in which there are 1 or 2 ring heteroatoms independently selected from O, N and S and wherein the heterocyclyl is optionally substituted on a ring carbon and/or (if present) on a ring nitrogen by 1 or 2 methyl groups; or heteroaryl-methyl- in which the heteroaryl is a 5-membered monocyclic heteroaromatic ring in which there are 1, 2 or 3 ring heteroatoms independently selected from O, N and S and wherein the heteroaryl is optionally substituted on the ring by 1 or 2 methyl groups; or $R^{3a}$ and $R^{3b}$, together with the carbon atom to which they are attached, form a 3-, 4-, 5- or 6-membered carbocyclic ring optionally substituted by 1 or 2 methyl groups; or $R^{3a}$ and $R^{3b}$ taken together are —$(CH_2)_n$—$X^3$—$(CH_2)_p$—, wherein $X^3$ is O, S, NH or NMe, and wherein n is 1, 2, 3 or 4 and p is 0, 1 or 2 provided that n+p is 2, 3 or 4; $R^4$ is of sub-formula (a) or (b):

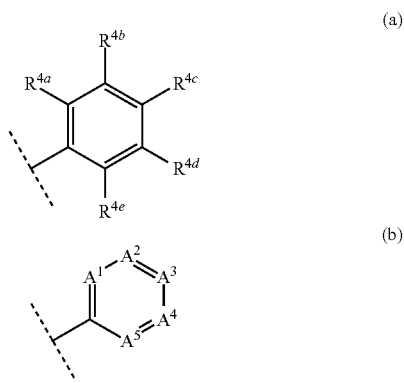

wherein, in sub-formula (a): $R^{4a}$ and $R^{4e}$ are independently hydrogen, halogen, $C_1$-$C_2$alkyl, $C_1$fluoroalkyl, hydroxy, $C_1$-$C_2$alkoxy, $C_1$fluoroalkoxy, methyl-$S(O)_2$—, $H_2N$—$S(O)_2$—, MeNH—$S(O)_2$—, or $Me_2N$—$S(O)_2$—; and $R^{4b}$, $R^{4c}$ and $R^{4d}$ are independently hydrogen, halogen, cyano, $C_1$-$C_4$alkyl, $C_1$-$C_2$fluoroalkyl, $C_1$-$C_3$alkoxy-$C_1$-$C_2$alkyl-, $C_1$fluoroalkoxy-$C_1$-$C_2$alkyl-, $MeOCH_2CH_2OCH_2$—, $C_3$-$C_6$cycloalkyl, hydroxy, $C_1$-$C_4$alkoxy, $C_1$-$C_2$fluoroalkoxy, thiol (HS—), $C_1$-$C_3$alkylthio-, $C_1$fluoroalkylthio-, $C_1$-$C_3$alkyl-S(O)—, $C_1$fluoroalkyl-S(O)—, $C_3$alkyl-$S(O)_2$—, $C_1$fluoroalkyl-$S(O)_2$—, $H_2N$—$S(O)_2$—, $C_1$-$C_4$alkyl-NH—$S(O)_2$—, $(C_1$-$C_3$alkyl)$_2$N—$S(O)_2$—, $C_1$-$C_4$alkyl-C(O)—, H—C(O)—, $C_1$-$C_3$alkoxy-C(O)—, HO—C(O)—, $H_2N$—C(O)—, $C_1$-$C_4$alkyl-NH—C(O)—, $(C_1$-$C_3$alkyl)$_2$N—C(O)—, (1-pyrrolidinyl)-C(O)—, (1-piperidinyl)-C(O)—, amino, $C_1$-$C_4$alkyl-NH—, $(C_1$-$C_3$alkyl)$_2$N—, 1-pyrrolidinyl, 1-piperidinyl, $C_1$-$C_4$alkyl-C(O)—NH—, H—C(O)—NH—, $C_1$-$C_3$alkyl-C(O)—N($C_1$-$C_3$alkyl)-, 2-oxo-1-pyrrolidinyl, 2-oxo-1-piperidinyl, $C_3$alkyl-$S(O)_2$—NH—, $C_1$-$C_3$alkyl-$S(O)_2$—N($C_1$-$C_3$alkyl)-, phenyl or phenyl substituted by one, two or three of $R^7$, or phenoxy or phenoxy substituted by one, two or three of $R^7$; provided that none of, or only one of, $R^{4b}$, $R^{4c}$ and $R^{4d}$ is $C_3$-$C_6$cycloalkyl, (1-pyrrolidinyl)-C(O)—, (1-piperidinyl)-C(O)—, 1-pyrrolidinyl, 1-piperidinyl, 2-oxo-1-pyrrolidinyl, 2-oxo-1-piperidinyl, phenyl, substituted phenyl, phenoxy or substituted phenoxy; wherein each $R^7$, independently of any other $R^7$, is fluorine, chlorine, $C_1$-$C_2$alkyl, $C_1$fluoroalkyl, $C_1$-$C_2$alkoxy or $C_1$fluoroalkoxy; and wherein, in sub-formula (b): $A^1$ is N or C—$R^{4f}$, $A^2$ is N or C—$R^{4g}$, $A^3$ is N or C—$R^{4h}$, $A^2$ is N or C—$R^{4i}$, and $A^5$ is N or C—$R^{4j}$, provided that one or two of $A^1$, $A^2$, $A^3$, $A^4$ and $A^5$ are nitrogen and the remaining ones of $A^1$, $A^2$, $A^3$, $A^4$ and $A^5$ are not nitrogen; wherein $R^{4f}$ and $R^{4j}$ are independently hydrogen, halogen, $C_1$-$C_2$alkyl, $C_1$fluoroalkyl, hydroxy (inclusive of any tautomer thereof), $C_1$-$C_2$alkoxy, or $C_1$fluoroalkoxy; and $R^{4g}$, $R^{4h}$ and $R^{4i}$ are independently hydrogen, halogen, $C_1$-$C_4$alkyl, $C_1$-$C_2$fluoroalkyl, $C_1$-$C_3$alkoxy-methyl-, $C_1$fluoroalkoxy-methyl-, $MeOCH_2CH_2OCH_2$—, $C_3$-$C_6$cycloalkyl, hydroxy (inclusive of any tautomer thereof), $C_1$-$C_4$alkoxy, $C_2$fluoroalkoxy, $C_1$-$C_4$alkyl-C(O)—, H—C(O)—, $C_1$-$C_3$alkoxy-C(O)—, HO—C(O)—, $H_2N$—C(O)—, $C_4$alkyl-NH—C(O)—, $(C_1$-$C_3$alkyl)$_2$N—C(O)—, (1-pyrrolidinyl)-C(O)—, (1-piperidinyl)-C(O)—, amino, $C_1$-$C_4$alkyl-NH—, $(C_1$-$C_3$alkyl$)_2$N—, 1-pyrrolidinyl, 1-piperidinyl, $C_1$-$C_4$alkyl-C(O)—NH—, H—C(O)—NH—, $C_1$-$C_3$alkyl-C(O)—N($C_1$-$C_3$alkyl)-, 2-oxo-1-pyrrolidinyl, 2-oxo-1-piperidinyl, phenyl or phenyl substituted by one, two or three of $R^7$, or phenoxy or phenoxy substituted by one, two or three of $R^7$; wherein $R^7$ is as defined hereinabove; provided that none of, or only one of, $R^{4g}$, $R^{4h}$ and $R^{4i}$ is $C_3$-$C_6$cycloalkyl, (1-pyrrolidinyl)-C(O)—, (1-piperidinyl)-C(O)—, 1-pyrrolidinyl, 1-piperidinyl, 2-oxo-1-pyrrolidinyl, 2-oxo-1-piperidinyl, phenyl, substituted phenyl, phenoxy or substituted phenoxy; and $R^5$ is hydroxy, $R^6$-oxy-, $R^8$—C(O)—O—, $C_1$-$C_{10}$alkyl-S(O)$_2$O—, $C_1$fluoroalky-S(O)$_2$O—, $C_1$chloroalkyl-S(O)$_2$O—, phenyl-S(O)$_2$O— or (4-methylphenyl)-S(O)$_2$O—; wherein $R^6$ is $C_1$-$C_{10}$alkyl, $C_1$-$C_4$-fluoroalkyl, $C_2$-$C_{10}$alkenyl, $C_2$-$C_{10}$alkynyl, $C_3$-$C_8$cycloalkyl, $C_3$-$C_8$cycloalkyl-$C_1$-$C_4$alkyl-, $C_1$-$C_4$alkoxy-CH$_2$CH$_2$—, $C_1$-$C_4$alkoxy-CH$_2$CH$_2$CH$_2$—, phenyl-$C_1$-$C_4$alkyl-, or phenyl-$C_1$-$C_4$alkyl- wherein the phenyl moiety is substituted by one, two or three $R^9$; $R^8$ is $C_1$-$C_{10}$alkyl, $C_1$-$C_4$-fluoroalkyl, $C_2$-$C_{10}$alkenyl, $C_2$-$C_{10}$alkynyl, $C_3$-$C_8$cycloalkyl, $C_3$-$C_8$cycloalkyl-$C_1$-$C_4$alkyl-, $C_1$-$C_4$alkoxy-$C_1$-$C_4$alkyl-, phenyl, phenyl substituted by one, two or three $R^9$, phenyl-$C_1$-$C_4$alkyl-, or phenyl-$C_1$-$C_4$alkyl- wherein the phenyl moiety is substituted by one, two or three $R^9$; or $R^8$ is $C_1$-$C_{10}$alkoxy, $C_1$-$C_4$-fluoroalkoxy, $C_1$-$C_{10}$alkenyloxy, $C_2$-$C_{10}$alkynyloxy, $C_3$-$C_8$cycloalkoxy, $C_3$-$C_8$cycloalkyl-$C_1$-$C_4$alkoxy-, $C_1$-$C_4$alkoxy-CH$_2$CH$_2$O—, $C_1$-$C_4$alkoxy-CH$_2$CH$_2$CH$_2$O—, phenoxy, phenoxy substituted by one, two or three $R^9$, phenyl-$C_1$-$C_4$alkoxy-, or phenyl-$C_1$-$C_4$alkoxy- wherein the phenyl moiety is substituted by one, two or three $R^9$; or $R^8$ is $C_1$-$C_{10}$alkylthio, $C_1$-$C_{10}$alkyl-NH—, or $(C_1$-$C_6$alkyl$)_2$N—; and wherein each $R^9$, independently of any other $R^9$, is fluorine, chlorine, $C_1$-$C_4$alkyl, $C_1$fluoroalkyl, $C_1$-$C_3$alkoxy or $C_1$fluoroalkoxy; or a salt (e.g. agriculturally acceptable salt) thereof.

In the description and claims of this specification, when references are made to a compound of formula (I), or to a compound of the invention, or to a compound (which is implicitly a compound of formula (I) or a compound of the invention), these references are intended to encompass the compound or a salt (e.g. agriculturally acceptable salt) thereof.

The compounds of formula (I) may exist in different geometric or optical isomers or tautomeric forms. The present invention covers all such isomers and tautomers and mixtures thereof in all proportions. Furthermore, it is possible that atropisomers are obtained in those cases where the rotation of the $R^4$ group is restricted, for example in those cases where the $R^4$ group (e.g. of sub-formula (a)) has at least one ortho-substituent, and all such atropisomers are included in the invention.

As an example of tautomerism, a compound of formula (Ia), i.e. a compound of formula (I) where $R^5$ is hydroxy, can be drawn in two tautomeric forms illustrated below, and the present invention covers each of these tautomeric forms as well as a mixture of these two tautomeric forms.

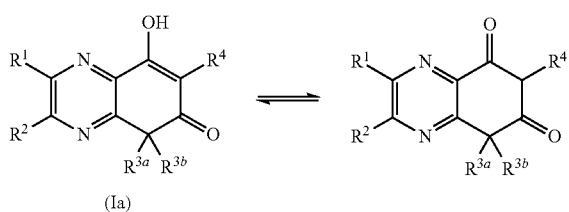

(Ia)

The compounds of formula (I) may contain one or more asymmetric carbon atoms, for example, at the —CR$^{3a}$R$^{3b}$— group, and may exist as enantiomers (or as pairs of diastereoisomers) or as mixtures of such, and all such isomers and mixtures of isomers are covered by the present invention.

Alkyl groups (either alone or as part of a larger group, such as alkoxy, alkoxy-carbonyl-, alkylcarbonyl-, et al.) can be in the form of a straight or branched chain. Typical examples are methyl, ethyl, propan-1-yl (n-propyl or propyl), propan-2-yl (isopropyl or 1-methylethyl), butan-1-yl (n-butyl or butyl), butan-2-yl (sec-butyl or 1-methylpropyl), 2-methylpropan-1-yl (isobutyl or 2-methylpropyl), or 2-methylpropan-2-yl (tert-butyl or 1,1-dimethylethyl). Except where more narrow ranges are stated, in general, alkyl groups are preferably $C_1$-$C_6$ alkyl, more preferably $C_1$-$C_4$ alkyl, most preferably $C_1$-$C_3$ alkyl groups.

Alkenyl groups (either alone or as part of a larger group, such as alkenyloxy) can be in the form of a straight or branched chain, and can be, where appropriate, of either the (E)- or (Z)-configuration. Typical examples are vinyl, allyl (prop-2-enyl) or 3-methyl-but-2-enyl. Except where more narrow ranges are stated, in general, alkenyl groups are preferably $C_2$-$C_6$, more preferably $C_2$-$C_4$, most preferably $C_2$-$C_3$ alkenyl groups.

Alkynyl groups (either alone or as part of a larger group, such as alkynyloxy) can be in the form of a straight or branched chain. Typical examples are ethynyl, propargyl (prop-2-ynyl) or but-2-ynyl. Except where more narrow ranges are stated, in general, alkynyl groups are preferably $C_2$-$C_6$, more preferably $C_2$-$C_4$, most preferably $C_2$-$C_3$ alkynyl groups.

Halogen is fluorine, chlorine, bromine or iodine. Preferably, e.g. in the compound of formula (I), halogen is fluorine, chlorine or bromine; such as fluorine or chlorine.

Fluoroalkyl groups (either alone or as part of a larger group, such as fluoroalkoxy or fluoroalkylthio-) are alkyl groups (straight-chain or branched) which are substituted by one or more (e.g. 1, 2 or 3) fluorine atoms. Typical examples are trifluoromethyl (CF$_3$), difluoromethyl, monofluoromethyl, 2,2,2-trifluoro-ethyl, 2,2-difluoro-ethyl (CHF$_2$CH$_2$—), 2-fluoro-ethyl or perfluorobutan-1-yl; in particular trifluoromethyl or 2,2,2-trifluoro-ethyl. Typical examples of fluoroalkoxy groups are difluoromethoxy, trifluoromethoxy, monofluoromethoxy, 2,2,2-trifluoro-ethoxy, 2,2-difluoro-ethoxy or 2-fluoro-ethoxy; in particular difluoromethoxy (CHF$_2$O).

Chloroalkyl groups (either alone or as part of a larger group, such as chloroalkoxy or chloroalkylthio-) are alkyl groups (straight-chain or branched) which are substituted by one or more (e.g. 1, 2 or 3) chlorine atoms. Typical examples are dichloromethyl, trichloromethyl or monochloromethyl, 2,2,2-trichloro-ethyl, 2,2-dichloro-ethyl, or 2-chloroethyl.

Fluoroalkenyl and chloroalkenyl groups are alkenyl groups which are substituted by one or more (e.g. 1, 2 or 3) fluorine or chlorine atoms respectively. Typical examples of fluoroalkenyl are 1-fluorovinyl, 2,2-difluoro-vinyl or 1,2,2-trifluoro-vinyl. Typical examples of chloroalkenyl are 1-chlorovinyl, 1,2-dichloro-vinyl, 2,2-dichloro-vinyl or 1,2,2-trichloro-vinyl.

Fluoroalkynyl and chloroalkynyl groups are alkynyl groups which are substituted by one or more (e.g. 1, 2 or 3) fluorine or chlorine atoms respectively. Typical examples of fluoroalkenyl are 1-fluoro-prop-2-ynyl, 1,1-difluoro-prop-2-ynyl or 3-fluoro-prop-2-ynyl. Typical examples of chloroalkynyl are 1-chloro-prop-2-ynyl or 3-chloro-prop-2-ynyl.

Cycloalkyl groups and carbocyclic rings (either alone or as part of a larger group, such as cycloalkyl-alkyl-) are monocyclic carbocycles. Typical examples are cyclopropyl, cyclobutyl, cyclopentyl or cyclohexyl. Except where more narrow ranges are stated, in general, cycloalkyl groups are preferably $C_3$-$C_6$, more preferably $C_3$-$C_5$ cycloalkyl groups.

Heterocyclyl groups and heterocyclic rings (either alone or as part of a larger group, such as heterocyclyl-alkyl-) are monocyclic saturated ring systems containing at least one ring heteroatom. Preferably, heterocyclyl groups will have one or two ring heteroatoms selected from nitrogen, oxygen and sulfur. Typical examples of heterocyclic groups include oxetanyl, tetrahydrofuranyl, tetrahydropyranyl, azetidinyl, pyrrolidinyl, piperidinyl, piperazinyl, morpholinyl, or thietanyl. Heterocyclyl groups having a single oxygen or nitrogen atom as the ring heteroatom are preferred. Except where more narrow ranges are stated, in general, heterocyclyl groups are preferably 4-, 5- or 6-membered rings, more preferably 5- or 6-membered rings.

Aryl groups (either alone or as part of a larger group, such as aryloxy- or arylthio-) are monocyclic or fused bicyclic aromatic ring systems. Examples of such rings include phenyl, naphthyl, or indenyl. The preferred aryl group is phenyl.

Heteroaryl groups (either alone or as part of a larger group, such as heteroaryloxy- or heteroarylthio-) are monocyclic or fused bicyclic aromatic ring systems containing at least one ring heteroatom. Preferably, single rings will have one, two or three heteroatoms selected from nitrogen, oxygen and sulfur. Typical examples of monocyclic heteroaryl groups are pyridyl, pyridazinyl, pyrimidinyl, pyrazinyl, triazinyl, pyrrolyl, pyrazolyl, imidazolyl, triazolyl, tetrazolyl, furanyl, thiophenyl, oxazolyl, isoxazolyl, oxadiazolyl, thiazolyl, isothiazolyl or thiadiazolyl. Preferably, bicyclic systems will have one, two, three or four ring heteroatoms selected from nitrogen, oxygen and sulfur. Typical examples of bicyclic heteroaryl groups are quinolinyl, cinnolinyl, quinoxalinyl, indolyl, indazolyl, benzimidazolyl, benzothiophenyl or benzothiadiazolyl. Monocyclic heteroaryl groups are preferred, and pyridyl is generally most preferred.

Where $R^5$ is other than hydroxy, the $R^5$ group is in most cases intended to be metabolised by a plant to a hydroxy group. In some cases, a $R^5$ group, which is other than hydroxy, might increase penetration of the compound of formula (I) into a plant, e.g. might increase penetration across the cuticle of the leaf of a plant, before metabolism by the plant of the $R^5$ group to a hydroxy group. Plant metabolism means the conversion or breakdown of a substance from one form to another by a plant (in planta).

Salts comprise a charged version of a compound of formula (I) and a counter ion of the opposite charge. The salt is preferably agriculturally acceptable. The compounds of formula (I) can have a negative charge, for example, on an oxygen atom of a hydroxy group, if the hydroxy group is deprotonated with a base (e.g. ammonia or an alkali metal hydroxide). Suitable cationic counter ions include, for example, alkali metals such as sodium or potassium, or alkaline earth metals such as magnesium or calcium, or quaternary ammonium such as ammonium or tetramethylammonium. Alternatively, the compounds of formula (I) can have a positive charge, for example, on the nitrogen atom in a nitrogen-containing heteroaryl group; for example: if the nitrogen atom is quaternised by protonation with an organic or inorganic acid, or if the nitrogen atom is quaternised by alkylation for example with a methyl group, or if the nitrogen atom is quaternised by amination. Suitable anionic counter ions include, for example, an anion of an organic acid, or an inorganic anion such as hydroxide, fluoride, chloride, bromide, iodide, sulfate, phosphate or nitrate.

The compounds of formula (I) according to the invention (encompassing a compound or a salt thereof) also include hydrates, which, for example, may be formed during salt formation.

Preferred, particular, suitable, typical or optional values, e.g. preferred, particular, suitable, typical or optional values of $R^1$, $R^2$, $R^{3a}$, $R^{3b}$, $R^4$, $R^5$, $R^6$, $R^7$, $R^8$ and $R^9$, et al., are as set out below, and these preferred features can be taken together in any combination.

Preferably $R^1$ is hydrogen, halogen, $C_1$-$C_3$alkyl (e.g. methyl or ethyl), $C_1$fluoroalkyl (e.g. $CF_3$), $C_1$-$C_2$alkoxy (e.g. methoxy) or $C_1$fluoroalkoxy (e.g. $CHF_2O$, $CF_3O$ or $CH_2FO$, in particular $CHF_2O$); more preferably hydrogen, fluorine, chlorine, methyl or ethyl; still more preferably hydrogen or methyl; most preferably hydrogen.

Preferably $R^2$ is hydrogen, halogen, $C_1$-$C_3$alkyl (e.g. methyl or ethyl), $C_1$fluoroalkyl (e.g. $CF_3$), $C_1$-$C_2$alkoxy (e.g. methoxy) or $C_1$fluoroalkoxy (e.g. $CHF_2O$, $CF_3O$ or $CH_2FO$, in particular $CHF_2O$); more preferably hydrogen, fluorine, chlorine, methyl or ethyl; still more preferably hydrogen or methyl; most preferably hydrogen.

Preferably, m is 1.

Preferably, when $R^{3a}$ and/or $R^{3b}$ are independently heterocyclyl-methyl-, then the heterocyclyl is a 4- or 5-membered saturated monocyclic heterocyclic ring linked by a ring carbon, in which there are 1 or 2 (in particular one) ring heteroatoms independently selected from O, N and S (in particular O), and wherein the heterocyclyl is unsubstituted or is substituted on a ring carbon and/or (if present) on a ring nitrogen by 1 or 2 methyl groups. Typical examples of the heterocyclyl-methyl- are: oxetan-3-yl-methyl-, oxetan-2-yl-methyl-, tetrahydrofuran-3-yl-methyl-, or tetrahydrofuran-2-yl-methyl-; or (when the heterocyclyl is a 5- or 6-membered monocyclic heterocyclic ring linked by a ring nitrogen) piperazin-1-yl-methyl-, 4-methyl-piperazin-1-yl-methyl-, pyrrolidin-1-yl-methyl-, or piperidin-1-yl-methyl-.

Preferably, when $R^{3a}$ and/or $R^{3b}$ are independently heteroaryl-methyl-, then the heteroaryl is a 5-membered monocyclic heteroaromatic ring in which there are 1 or 2 (e.g. 1) ring heteroatoms independently selected from O, N and S (e.g. selected from O and N) and wherein the heteroaryl is unsubstituted or is substituted on the ring by 1 or 2 (e.g. 1) methyl groups; in particular unsubstituted or substituted furanyl-methyl-. Typical examples of the heteroaryl-methyl- are furan-3-yl-methyl- or furan-2-yl-methyl-.

Preferably, when $R^{3a}$ and $R^{3b}$, together with the carbon atom to which they are attached, form a 3-, 4-, 5- or 6-membered carbocyclic ring optionally substituted by 1 or 2 methyl groups, then preferably they form a 3-, 4- or 5- (e.g. 3- or 4-) membered optionally substituted carbocyclic ring; and more preferably they form an unsubstituted cyclopropyl ring.

In a particular embodiment, $X^3$ is O, NH or NMe; more particularly O.

In a particular embodiment, n is 1, 2 or 3 and p is 0 or 1 provided that n+p is 2 or 3.

Preferably, neither $R^{3a}$ nor $R^{3b}$ is hydrogen. This avoids or minimizes possible aromatization of the right-hand, carbocyclic, ring illustrated in formula (I).

Preferably $R^{3a}$ is $C_1$-$C_4$alkyl, $C_1$-$C_3$-fluoroalkyl (e.g. $C_1$fluoroalkyl-$CH_2$—), $C_2$-$C_3$alkenyl, $C_2$-$C_3$-fluoroalkenyl, $C_2$chloroalkenyl (e.g. 1-chloro-vinyl), $C_2$-$C_3$alkynyl, $C_3$-$C_5$cycloalkyl, $C_3$-$C_4$cycloalkyl-$CH_2$—, or phenyl. More preferably, $R^{3a}$ is methyl, ethyl, n-propyl, isopropyl, $C_1$fluoroalkyl-$CH_2$— (e.g. 2-fluoro-ethyl, 2,2-difluoro-ethyl or 2,2,2-trifluoro-ethyl), vinyl, allyl, $C_2$fluoroalkenyl (e.g. 2,2-difluoro-vinyl or 1,2,2-trifluoro-vinyl), propargyl, cyclopropyl, cyclobutyl, cyclopentyl, cyclopropyl-methyl-, or phenyl. Still more preferably, $R^{3a}$ is methyl, ethyl, $C_1$fluoroalkyl-$CH_2$— (e.g. 2-fluoro-ethyl, 2,2-difluoro-ethyl ($CHF_2CH_2$—), or 2,2,2-trifluoro-ethyl), vinyl, allyl, 2,2-difluoro-vinyl, 1,2,2-trifluoro-vinyl, propargyl, cyclopropyl, cyclobutyl, cyclopentyl, or cyclopropyl-methyl-. Most preferably, $R^{3a}$ is methyl.

Preferably $R^{3b}$ is $C_1$-$C_4$alkyl, $C_1$-$C_3$-fluoroalkyl (e.g. $C_1$fluoroalkyl-$CH_2$—), $C_2$-$C_3$alkenyl, $C_2$-$C_3$-fluoroalkenyl, $C_2$chloroalkenyl (e.g. 1-chloro-vinyl), $C_2$-$C_3$alkynyl, $C_3$-$C_5$cycloalkyl, $C_3$-$C_4$cycloalkyl-$CH_2$—, or phenyl. More preferably, $R^{3b}$ is methyl, ethyl, n-propyl, isopropyl, $C_1$fluoroalkyl-$CH_2$— (e.g. 2-fluoro-ethyl, 2,2-difluoro-ethyl or 2,2,2-trifluoro-ethyl), vinyl, allyl, $C_2$fluoroalkenyl (e.g. 2,2-difluoro-vinyl or 1,2,2-trifluoro-vinyl), propargyl, cyclopropyl, cyclobutyl, cyclopentyl, cyclopropyl-methyl-, or phenyl. Still more preferably, $R^{3b}$ is methyl, ethyl, $C_1$fluoroalkyl-$CH_2$— (e.g. 2-fluoro-ethyl, 2,2-difluoro-ethyl or 2,2,2-trifluoro-ethyl), vinyl, allyl, 2,2-difluoro-vinyl, 1,2,2-trifluoro-vinyl, propargyl, cyclopropyl, cyclobutyl, cyclopentyl, or cyclopropyl-methyl-. Yet more preferably, $R^{3b}$ is methyl, ethyl, $C_1$fluoroalkyl-$CH_2$— (e.g. 2-fluoro-ethyl, 2,2-difluoro-ethyl ($CHF_2CH_2$—), or 2,2,2-trifluoro-ethyl), vinyl, allyl or propargyl; in particular methyl.

Most preferably, $R^{3a}$ is methyl and $R^{3b}$ is as defined in one of the above-mentioned preferable definitions of $R^{3b}$.

In an alternative preferred embodiment, $R^{3a}$ and $R^{3b}$, together with the carbon atom to which they are attached, form an unsubstituted cyclopropyl, cyclobutyl or cyclopentyl (in particular cyclopropyl) ring.

In one preferred embodiment both $R^{3a}$ and $R^{3b}$ are methyl.
In one preferred embodiment $R^{3a}$ is methyl and $R^{3b}$ is ethyl.
In one preferred embodiment $R^{3a}$ is methyl and $R^{3b}$ is 2,2-difluoro-ethyl ($CHF_2CH_2$—).
In one preferred embodiment $R^{3a}$ is methyl and $R^{3b}$ is 2,2,2-trifluoro-ethyl ($CF_3CH_2$—).
In one preferred embodiment $R^{3a}$ is methyl and $R^{3b}$ is vinyl.
In one preferred embodiment $R^{3a}$ is methyl and $R^{3b}$ is allyl.
In one preferred embodiment $R^{3a}$ is methyl and $R^{3b}$ is propargyl.
In one preferred embodiment $R^{3a}$ and $R^{3b}$, together with the carbon atom to which they are attached, form an unsubstituted cyclopropyl ring.
In one particular embodiment $R^{3a}$ is methyl and $R^{3b}$ is cyclopentyl.
In one particular embodiment $R^{3a}$ is methyl and $R^{3b}$ is phenyl.
In one particular embodiment both $R^{3a}$ and $R^{3b}$ are allyl.
In one particular embodiment both $R^{3a}$ and $R^{3b}$ are cyclopentyl.

In $R^4$, sub-formula (a), preferable features are as follows.
Preferably, at least one of $R^{4a}$ and $R^{4e}$ is not hydrogen or fluorine.

Preferably, $R^{4a}$ and $R^{4e}$ are independently hydrogen, fluorine, chlorine, bromine, iodine, methyl, ethyl, $C_1$fluoroalkyl (e.g. $CF_3$), methoxy, $C_1$fluoroalkoxy (e.g. $CHF_2O$, $CF_3O$ or $CH_2FO$, in particular $CHF_2O$), methyl-$S(O)_2$— or $H_2N$—$S(O)_2$—. More preferably, $R^{4a}$ and $R^{4e}$ are independently hydrogen, fluorine, chlorine, bromine, methyl, $C_1$fluoroalkyl (e.g. $CF_3$), methoxy, $C_1$fluoroalkoxy (e.g. $CHF_2O$, $CF_3O$ or $CH_2FO$, in particular $CHF_2O$), or methyl-$S(O)_2$—. Still more preferably, $R^{4a}$ and $R^{4e}$ are independently hydrogen, fluorine, chlorine, bromine, methyl, $CF_3$ or methoxy. Preferably, in these cases, at least one of $R^{4a}$ and $R^{4e}$ is not hydrogen or fluorine.

Most preferably, $R^{4a}$ is chlorine; in which case preferably $R^{4e}$ is hydrogen, fluorine, chlorine, bromine, methyl, $CF_3$ or methoxy.

Preferably, $R^{4b}$, $R^{4c}$ and $R^{4d}$ are independently hydrogen, halogen (fluorine, chlorine, bromine or iodine), $C_1$-$C_4$alkyl (e.g. methyl or ethyl), $C_1$fluoroalkyl (e.g. $CF_3$), methoxymethyl-, $MeOCH_2CH_2OCH_2$—, $C_3$-$C_5$cycloalkyl (e.g. cyclopropyl), $C_1$-$C_3$alkoxy (e.g. methoxy or ethoxy), $C_1$fluoroalkoxy (such as $CHF_2O$, $CF_3O$ or $CH_2FO$, in particular $CHF_2O$), $C_1$-$C_3$alkyl-$S(O)_2$— (e.g. methyl-$S(O)_2$—), $H_2N$—$S(O)_2$—, $C_1$-$C_3$alkyl-NH—$S(O)_2$— (e.g. MeNH—$S(O)_2$—), or $(C_1$-$C_3$alkyl$)_2N$—$S(O)_2$— (e.g. $Me_2N$—$S(O)_2$—); or phenyl or phenyl substituted by one or two of $R^7$, wherein each $R^7$, independently of any other $R^7$, is fluorine, chlorine, methyl, $C_1$fluoroalkyl (e.g. $CF_3$), methoxy or $C_1$fluoroalkoxy (e.g. $CHF_2O$, $CF_3O$ or $CH_2FO$, in particular $CHF_2O$); provided that none of, or only one of, $R^{4b}$, $R^{4c}$ and $R^{4d}$ is $C_3$-$C_5$cycloalkyl, phenyl or substituted phenyl.

More preferably, $R^{4b}$, $R^{4c}$ and $R^{4d}$ are independently hydrogen, fluorine, chlorine, bromine, methyl, ethyl, $C_1$fluoroalkyl (e.g. $CF_3$), cyclopropyl, methoxy, ethoxy, $C_1$fluoroalkoxy (such as $CHF_2O$, $CF_3O$ or $CH_2FO$, in particular $CHF_2O$), or methyl-$S(O)_2$—; or phenyl or phenyl substituted by one or two (e.g. one) of $R^7$, wherein each $R^7$, independently of any other $R^7$, is fluorine, chlorine, methyl, $CF_3$, methoxy, $CHF_2O$ or $CH_2FO$;
provided that none of, or only one of, $R^{4b}$, $R^{4c}$ and $R^{4d}$ is cyclopropyl, phenyl or substituted phenyl.

Still more preferably, $R^{4b}$, $R^{4c}$ and $R^{4d}$ are independently hydrogen, fluorine, chlorine, bromine, methyl, ethyl, $C_1$fluoroalkyl (e.g. $CF_3$), cyclopropyl, methoxy, $C_1$fluoroalkoxy (such as $CHF_2O$, $CF_3O$ or $CH_2FO$, in particular $CHF_2O$), or methyl-$S(O)_2$—;
provided that none of, or only one of, $R^{4b}$, $R^{4c}$ and $R^{4d}$ is cyclopropyl.

Preferably, one or two (e.g. two) of $R^{4b}$, $R^{4c}$ and $R^{4d}$ are hydrogen.

Preferably, in $R^4$ sub-formula (a) or (b), $R^7$, independently of any other $R^7$, is fluorine, chlorine, methyl, $C_1$fluoroalkyl (e.g. $CF_3$), methoxy or $C_1$fluoroalkoxy (e.g. $CHF_2O$, $CF_3O$ or $CH_2FO$, in particular $CHF_2O$).

In one particular embodiment $R^4$ is 2-trifluoromethyl-phenyl-.
In one particular embodiment $R^4$ is 2-chloro-phenyl-.
In one particular embodiment $R^4$ is 2-bromo-phenyl-.
In one particular embodiment $R^4$ is 2-methyl-phenyl-.
In one particular embodiment $R^4$ is 2-methoxy-phenyl-.
In one particular embodiment $R^4$ is 2,4-difluoro-phenyl-.
In one particular embodiment $R^4$ is 2,6-dichloro-phenyl-.
In one particular embodiment $R^4$ is 2,3-dichloro-6-fluoro-phenyl-.
In one particular embodiment $R^4$ is 2-chloro-3,6-difluoro-phenyl-.
In one particular embodiment $R^4$ is 3-bromo-2-chloro-6-fluoro-phenyl-.
In one particular embodiment $R^4$ is 2,3,6-trichloro-phenyl-.
In one particular embodiment $R^4$ is 2-chloro-5-trifluoromethyl-phenyl-.
In one particular embodiment $R^4$ is 2-chloro-6-trifluoromethyl-phenyl-.
In one particular embodiment $R^4$ is 2,5-bis-(trifluoromethyl)-phenyl-.
In one particular embodiment $R^4$ is 2-bromo-5-chloro-phenyl-.
In one particular embodiment $R^4$ is 4-bromo-2-trifluoromethyl-phenyl-.
In one particular embodiment $R^4$ is 4-chloro-2-methylsulfonyl-phenyl-.
In one particular embodiment $R^4$ is 4-chloro-2-trifluoromethyl-phenyl-.

In one particular embodiment $R^4$ is 5-chloro-2-trifluoromethyl-phenyl-.

In one particular embodiment $R^4$ is 3,5-difluoro-2-trifluoromethyl-phenyl-.

In one particular embodiment $R^4$ is 2-ethyl-4-(4'-chlorophenyl)-phenyl-.

In one particular embodiment $R^4$ is 2,4,6-trimethyl-phenyl-.

In one embodiment $R^4$ is 4-chloro-phenyl-.

In one embodiment $R^4$ is 3-trifluoromethyl-phenyl-.

In $R^4$, sub-formula (b), preferable features are as follows.

Preferably, one of $A^1$, $A^2$, $A^3$, $A^4$ and $A^5$ is nitrogen and the remaining ones of $A^1$, $A^2$, $A^3$, $A^4$ and $A^5$ are not nitrogen. That is, in $R^4$, sub-formula (b) is preferably pyridinyl or substituted pyridinyl.

In one particular embodiment, $A^1$ is nitrogen and $A^2$, $A^3$, $A^4$ and $A^5$ are not nitrogen. That is, in $R^4$, sub-formula (b) is particularly pyridin-2-yl or substituted pyridin-2-yl.

In one particular embodiment, $A^2$ is nitrogen and $A^1$, $A^3$, $A^4$ and $A^5$ are not nitrogen. That is, in $R^4$, sub-formula (b) is particularly pyridin-3-yl or substituted pyridin-3-yl.

In one particular embodiment, $A^3$ is nitrogen and $A^1$, $A^2$, $A^4$ and $A^5$ are not nitrogen. That is, in $R^4$, sub-formula (b) is particularly pyridin-4-yl or substituted pyridin-4-yl.

Preferably, at least one of $R^{4f}$ and $R^{4j}$ is not hydrogen or fluorine.

Preferably, $R^{4f}$ and $R^{4j}$ are independently hydrogen, fluorine, chlorine, methyl, $C_1$fluoroalkyl (e.g. $CF_3$), or hydroxy (inclusive of any tautomer thereof). More preferably, $R^{4f}$ and $R^{4j}$ are independently hydrogen, fluorine, chlorine, methyl or $C_1$fluoroalkyl (e.g. $CF_3$). Still more preferably, $R^{4f}$ and $R^{4j}$ are independently hydrogen, chlorine or $CF_3$. Preferably, in these cases, at least one of $R^{4f}$ and $R^{4j}$ is not hydrogen or fluorine.

More preferably, one of $R^{4f}$ and $R^{4j}$ is chlorine. In this case, preferably, the other of $R^{4f}$ and $R^{4j}$ is hydrogen, fluorine, chlorine, methyl, $C_1$fluoroalkyl (e.g. $CF_3$), or hydroxy (inclusive of any tautomer thereof); or more preferably the other of $R^{4f}$ and $R^{4j}$ is hydrogen, fluorine, chlorine, methyl or $C_1$fluoroalkyl (e.g. $CF_3$); or still more preferably the other of $R^{4f}$ and $R^{4j}$ is hydrogen, chlorine or $CF_3$.

Preferably, $R^{4g}$, $R^{4h}$ and $R^{4i}$ are independently hydrogen, fluorine, chlorine, $C_1$-$C_4$alkyl (e.g. methyl or ethyl), $C_1$fluoroalkyl (e.g. $CF_3$), methoxymethyl-, $MeOCH_2CH_2OCH_2$—, $C_3$-$C_5$cycloalkyl (e.g. cyclopropyl), hydroxy (inclusive of any tautomer thereof); $C_1$-$C_3$alkoxy (e.g. methoxy or ethoxy), or $C_1$fluoroalkoxy (such as $CHF_2O$, $CF_3O$ or $CH_2FO$, in particular $CHF_2O$); or phenyl or phenyl substituted by one, two or three of $R^7$, wherein $R^7$, independently of any other $R^7$, is fluorine, chlorine, methyl, $C_1$fluoroalkyl (e.g. $CF_3$), methoxy or $C_1$fluoroalkoxy (e.g. $CHF_2O$, $CF_3O$ or $CH_2FO$, in particular $CHF_2O$);
provided that none of, or only one of, $R^{4g}$, $R^{4h}$ and $R^{4i}$ is $C_3$-$C_5$cycloalkyl, phenyl or substituted phenyl.

More preferably, $R^{4g}$, $R^{4h}$ and $R^{4i}$ are independently hydrogen, fluorine, chlorine, methyl, or $C_1$fluoroalkyl (e.g. $CF_3$).

Preferably, one or two (e.g. two) of $R^{4g}$, $R^{4h}$ and $R^{4i}$ are hydrogen.

Preferable examples of groups for $R^4$, sub-formula (b), are 3,5-dichloro-pyridin-2-yl, 3,6-dichloro-pyridin-2-yl, 3-chloro-5-fluoro-pyridin-2-yl, 3-chloro-5-trifluoromethyl-pyridin-2-yl, 3,5,6-trichloro-pyridin-2-yl, 2,4-dichloro-pyridin-3-yl, 2,5-dichloro-pyridin-3-yl, 2,6-dichloro-pyridin-3-yl, 4,6-dichloro-pyridin-3-yl, 2-chloro-4-trifluoromethyl-pyridin-3-yl, 2-chloro-6-trifluoromethyl-pyridin-3-yl, 2-hydroxy-pyridin-3-yl (inclusive of its pyridone tautomer), 2,3-dichloro-pyridin-4-yl, 2,5-dichloro-pyridin-4-yl, 3,5-dichloro-pyridin-4-yl, 3-chloro-5-trifluoromethyl-pyridin-4-yl, 2,3,5-trichloro-pyridin-4-yl, or 5-chloro-pyrimidin-4-yl.

Alternative particular examples of groups for $R^4$, sub-formula (b), are 6-hydroxy-pyridin-2-yl 6-hydroxy-pyridin-3-yl, or 2-hydroxy-pyridin-4-yl (all inclusive of their pyridone tautomers).

When $R^5$ is $C_1$-$C_{10}$alkyl-$S(O)_2O$—, $C_1$fluoroalkyl-$S(O)_2O$—, $C_1$chloroalkyl-$S(O)_2O$—, phenyl-$S(O)_2O$— or (4-methyl-phenyl)-$S(O)_2O$—, then it can for example be methanesulfonyloxy-, ethanesulfonyloxy-, trifluoromethanesulfonyloxy-, trichloromethanesulfonyloxy-, benzenesulfonyloxy- or para-toluenesulfonyloxy-.

Preferably, $R^5$ is hydroxy, $R^6$-oxy- or $R^8$—C(O)—O—.

More preferably, $R^5$ is hydroxy or $R^8$—C(O)—O—.

Preferably, $R^6$ is $C_1$-$C_8$alkyl (e.g. $C_1$-$C_6$alkyl, such as $C_1$-$C_4$alkyl), $C_1$-$C_2$fluoroalkyl, $C_2$-$C_5$alkenyl-$CH_2$— (e.g. allyl), $C_2$-$C_5$alkynyl-$CH_2$— (e.g. propargyl), $C_3$-$C_6$cycloalkyl, $C_3$-$C_6$cycloalkyl-$C_1$-$C_2$alkyl-, $C_1$-$C_2$alkoxy-$CH_2CH_2$—, $C_1$-$C_2$alkoxy-$CH_2CH_2CH_2$—, phenyl-$C_1$-$C_2$alkyl-, or phenyl-$C_1$-$C_2$alkyl- wherein the phenyl moiety is substituted by one or two $R^9$; and wherein each $R^9$, independently of any other $R^9$, is fluorine, chlorine, $C_1$-$C_2$alkyl, $C_1$fluoroalkyl, $C_1$-$C_2$alkoxy or $C_1$fluoroalkoxy.

In one particular embodiment, $R^5$ is $R^6$-oxy- and is: methoxy, ethoxy, n-propoxy, isopropoxy, n-butoxy, tert-butoxy, allyloxy, propargyloxy, or benzyloxy.

Preferably, $R^8$ is $C_1$-$C_8$alkyl (e.g. $C_1$-$C_6$alkyl, such as $C_2$-$C_4$alkyl, e.g. isopropyl or tert-butyl), $C_1$-$C_2$fluoroalkyl (e.g. $C_1$fluoroalkyl), $C_2$-$C_6$alkenyl, $C_2$-$C_6$alkynyl, $C_3$-$C_6$cycloalkyl, $C_3$-$C_6$cycloalkyl-$C_1$-$C_2$alkyl-, $C_1$-$C_2$alkoxy-$CH_2$—, $C_1$-$C_2$alkoxy-$CH_2CH_2$—, $C_1$-$C_2$alkoxy-$CH_2CH_2CH_2$—, phenyl-$C_1$-$C_2$alkyl-, or phenyl-$C_1$-$C_2$alkyl- wherein the phenyl moiety is substituted by one or two $R^9$; or $R^8$ is $C_1$-$C_8$alkoxy (e.g. $C_1$-$C_6$alkoxy, such as $C_1$-$C_4$alkoxy, e.g. methoxy or ethoxy), $C_1$-$C_2$fluoroalkoxy (e.g. $C_1$fluoroalkoxy), $C_2$-$C_5$alkenyl-$CH_2$-oxy (e.g. allyloxy), $C_2$-$C_5$alkynyl-$CH_2$-oxy (e.g. propargyloxy), $C_3$-$C_6$cycloalkoxy, $C_3$-$C_6$cycloalkyl-$C_1$-$C_2$alkoxy-, $C_1$-$C_2$alkoxy-$CH_2CH_2O$—, $C_1$-$C_2$alkoxy-$CH_2CH_2CH_2O$—, phenoxy, phenoxy substituted by one, two or three $R^9$, phenyl-$C_1$-$C_2$alkoxy-, or phenyl-$C_1$-$C_2$alkoxy- wherein the phenyl moiety is substituted by one or two $R^9$; or $R^8$ is $C_1$-$C_6$alkylthio-, $C_1$-$C_6$alkyl-NH—, or $(C_1$-$C_4$alkyl$)_2$N—; and wherein each $R^9$, independently of any other $R^9$, is fluorine, chlorine, methyl, ethyl, $C_1$fluoroalkyl (e.g. trifluoromethyl), methoxy or $C_1$fluoroalkoxy (e.g. difluoromethoxy or trifluoromethoxy).

More preferably, $R^8$ is $C_1$-$C_8$alkyl (in particular $C_1$-$C_6$alkyl, such as $C_2$-$C_4$alkyl, e.g. isopropyl or tert-butyl) or $C_1$-$C_8$alkoxy (e.g. $C_1$-$C_6$alkoxy, such as $C_1$-$C_4$alkoxy, e.g. methoxy or ethoxy).

Most preferably, $R^8$ is $C_1$-$C_8$alkyl (in particular $C_1$-$C_6$alkyl, such as $C_2$-$C_4$alkyl, e.g. isopropyl or tert-butyl).

In one particularly preferred embodiment, $R^5$ is $R^8$—C(O)—O— and is: propan-2-ylcarbonyloxy-(isopropylcarbonyloxy-), 2-methyl-propan-2-ylcarbonyloxy-(tert-butylcarbonyloxy-), methoxycarbonyloxy-, ethoxycarbonyloxy-, or ethylthiocarbonyloxy-.

In one even more particularly preferred embodiment, $R^5$ is $R^8$—C(O)—O— and is: propan-2-ylcarbonyloxy-(isopropylcarbonyloxy-) or 2-methyl-propan-2-ylcarbonyloxy-(tert-butylcarbonyloxy-).

In an alternative particularly preferred embodiment, $R^5$ is hydroxy.

Preferably, the compound of formula (I) is one of compounds E1, E2, E3, E4, E5, E6, E7, F1, F2, F3, F4, F5, or F6, which have the structures shown in Example 2.4 Table E and/or Example 2.5 Table F hereinafter, or an agriculturally acceptable salt thereof.

More preferably, the compound of formula (I) is one of compounds E1, E2, E3, E4, E5, F1, F2, F3 or F4, which have the structures shown in Example 2.4 Table E and/or Example 2.5 Table F hereinafter, or an agriculturally acceptable salt thereof.

Certain intermediates, useable in a process for preparing a compound of formula (I), are thought to be novel, and thus form other aspects of the present invention.

Thus, a further aspect of the present invention provides a compound of formula (8):

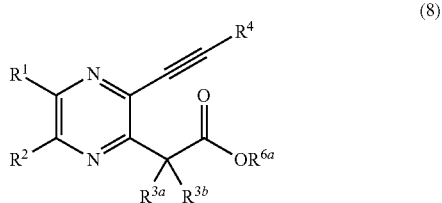

(8)

wherein $R^1$, $R^2$, $R^{3a}$, $R^{3b}$ and $R^4$ are as defined for the compound of formula (I) and $R^{6a}$ is $C_1$-$C_4$ alkyl. Preferably, $R^1$ and $R^2$ are both hydrogen. Suitably, $R^{6a}$ is methyl, ethyl, n-propyl, isopropyl or n-butyl, or more preferably methyl or ethyl.

A yet further aspect of the present invention provides a compound of formula (10):

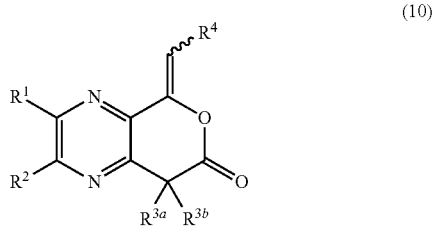

(10)

wherein $R^1$, $R^2$, $R^{3a}$, $R^{3b}$ and $R^4$ are as defined for the compound of formula (I). Preferably, $R^1$ and $R^2$ are both hydrogen.

Processes for Preparing the Compound of Formula (I)

A first part of a process for preparing a compound of formula (I), namely preparing an intermediate compound of formula (6), is shown in Scheme 1 below.

The steps of Scheme 1 are as follows:

1. A malonate compound of formula (3) wherein $R^1$ and $R^2$ are as defined for a compound of formula (I) and $R^{6a}$ is $C_1$-$C_4$ alkyl can be prepared by reacting a 2,3-dichloropyrazine of formula (2) wherein $R^1$ and $R^2$ are as defined for a compound of formula (I). The reaction can be carried out using a malonate ester of formula (7) with a base, such as sodium or potassium carbonate, in a non-aqueous (e.g. anhydrous) organic solvent, such as N,N-dimethylformamide (DMF) or N-methyl-pyrrolidinone (NMP). Suitably, $R^{6a}$ is methyl, ethyl, n-propyl, isopropyl or n-butyl, or more preferably methyl or ethyl. Suitably, the reaction to prepare the malonate compound of formula (3) is heated at 50 to 170° C., e.g. 80 to 140° C., such as about 100-120° C. Malonates of formula (7) are commercially available and/or can be prepared by methods known to the person skilled in the art.

2. A carboxylic acid of formula (4) wherein $R^1$ and $R^2$ are as defined for a compound of formula (I) can be prepared by reacting an aqueous solution of a hydroxide salt (such as an alkali metal hydroxide, e.g. NaOH or KOH, or an alkaline earth metal hydroxide) with a malonate compound of formula (3) where $R^1$ and $R^2$ are as defined for a compound of formula (I), in a solvent, such as ethanol and/or methanol. Suitably, the reaction temperature for preparing the carboxylic acid of formula (4) is 40 to 100° C., e.g. 50 to 90° C., such as about 60-80° C.

Scheme 1

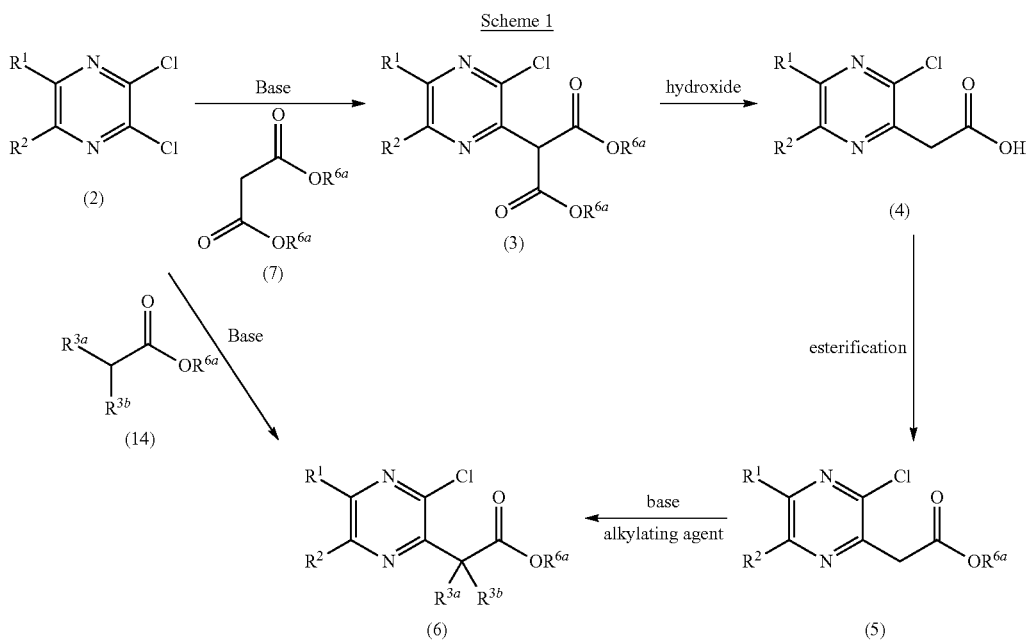

3. An ester of formula (5), wherein $R^1$ and $R^2$ are as defined for a compound of formula (I), and wherein $R^{6a}$ is $C_1$-$C_4$alkyl such as methyl, ethyl, n-propyl, isopropyl or n-butyl, or more preferably methyl or ethyl, can be prepared by reacting an acid of formula (4) where $R^1$ and $R^2$ are as defined for a compound of formula (1) with an activating agent, such as 1,1'-carbonyldiimidazole, in the presence of an alcohol $R^{6a}$—OH, preferably methanol or ethanol, in a solvent such as N,N-dimethylformamide.

4. An ester of formula (6), wherein $R^1$ and $R^2$ are as defined for a compound of formula (I), and wherein $R^{6a}$ is $C_1$-$C_4$alkyl such as methyl, ethyl, n-propyl, isopropyl or n-butyl, or more preferably methyl or ethyl, can be prepared by reacting an ester of formula (5), wherein $R^1$ and $R^2$ are as defined for a compound of formula (I) and $R^{6a}$ is $C_1$-$C_4$alkyl, with alkylating agents $R^{3a}$—$X^{3a}$ and $R^{3b}$—$X^{3b}$, wherein $X^{3a}$ and $X^{3b}$ are independently a leaving group, in the presence of a base, preferably a lithium amide base, in a non-aqueous (e.g. anhydrous) organic solvent, such as N,N-dimethylformamide (DMF) and/or tetrahydrofuran. Preferably, $X^{3a}$ and $X^{3b}$ are independently iodine, bromine, chlorine, p-toluenesulfonate, benzenesulfonate, methanesulfonate or trifluoromethanesulfonate. It is noted that $R^{3a}$—$X^{3a}$ and $R^{3b}$—$X^{3b}$ can be the same single alkylating agent when $R^{3a}$=$R^{3b}$; for example, when $R^{3a}$=$R^{3b}$=methyl then preferably $R^{3a}$—$X^{3a}$ and $R^{3b}$—$X^{3b}$ are both methyl iodide. Preferably, the lithium amide base is lithium hexamethyldisilazide (LHMDS), lithium diisopropylamide (LDA) or lithium dimethylamide. The reaction temperature can for example be –20 to 30° C. such as 0 to 25° C.

1A. In an alternative shorter route, an ester of formula (6) where $R^1$ and $R^2$ are as defined for a compound of formula (I) can be prepared by reacting an ester of formula (14) with a 2,3-dichloropyrazine of formula (2) (wherein $R^1$ and $R^2$ are as defined for a compound of formula (I)), in the presence of a base, preferably a lithium amide base such as lithium hexamethyldisilazide (LHMDS) or lithium diisopropylamide (LDA) or lithium dimethylamide, in a non-aqueous (e.g. anhydrous) organic solvent, such as tetrahydrofuran and/or N,N-dimethylformamide (DMF). The reaction temperature can for example be –20 to 30° C. such as 0 to 25° C. The ester of formula (14) can for example be: 2-methyl butyric acid methyl ester ($CH_3CH_2$—CH(Me)-C(O)OMe), for when $R^{3a}$=methyl and $R^{3b}$=ethyl; or the methyl or ethyl ester of isobutyric acid ($Me_2CH$—C(O)OMe or $Me_2CH$—C(O)OEt), for when $R^{3a}$ and $R^{3b}$ are both methyl.

A second part of a process for preparing a compound of formula (I), namely converting an intermediate compound of formula (6) into a compound of formula (I), is shown in Scheme 2 below.

The subsequent steps, in Scheme 2 are as follows:

5. An alkyne ester of formula (8), wherein $R^1$, $R^2$, $R^{3a}$, $R^{3b}$ and $R^4$ are as defined for a compound of formula (I), and wherein $R^{6a}$ is $C_1$-$C_4$alkyl such as methyl, ethyl, n-propyl, isopropyl or n-butyl, or more preferably methyl or ethyl, can be prepared by reacting an ester of formula (6) wherein $R^1$, $R^2$, $R^{3a}$ and $R^{3b}$ are as defined for a compound of formula (I) and having the same $R^{6a}$ group, with an alkyne of formula (13) in the presence of a base, such as an alkali metal carbonate such as caesium carbonate (e.g. in solid form), a palladium catalyst, such as (1,1'-bis(diphenylphosphino)-ferrocene) dichloro palladium(2), a phosphine, such as 4,5-(bisdiphenylphosphino)-9,9-dimethylxanthene ("Xantphos") or triphenylphosphine, in a non-aqueous (e.g. anhydrous) organic solvent, such as acetonitrile, for example under an inert (e.g. nitrogen) atmosphere. Suitably, the reaction temperature is 60 to 100° C. (e.g. 70 to 80° C.) and/or the reflux temperature of the organic solvent used.

6. A carboxylic acid of formula (9) where $R^1$, $R^2$, $R^{3a}$, $R^{3b}$ and $R^4$ are as defined for a compound of formula (I) can be prepared by reacting an alkyne ester of formula (8), wherein $R^1$, $R^2$, $R^{3a}$, $R^{3b}$ and $R^4$ are as defined for a compound of formula (I) and $R^{6a}$ is $C_1$-$C_4$alkyl e.g. Me or Et, with an aqueous solution of a hydroxide salt (such as an alkali metal hydroxide, e.g. NaOH or KOH, or an alkaline earth metal hydroxide), in a solvent, such as ethanol and/or methanol. Suitably, the reaction temperature is 40 to 100° C., e.g. 50 to 90° C., such as about 60-80° C.

Scheme 2

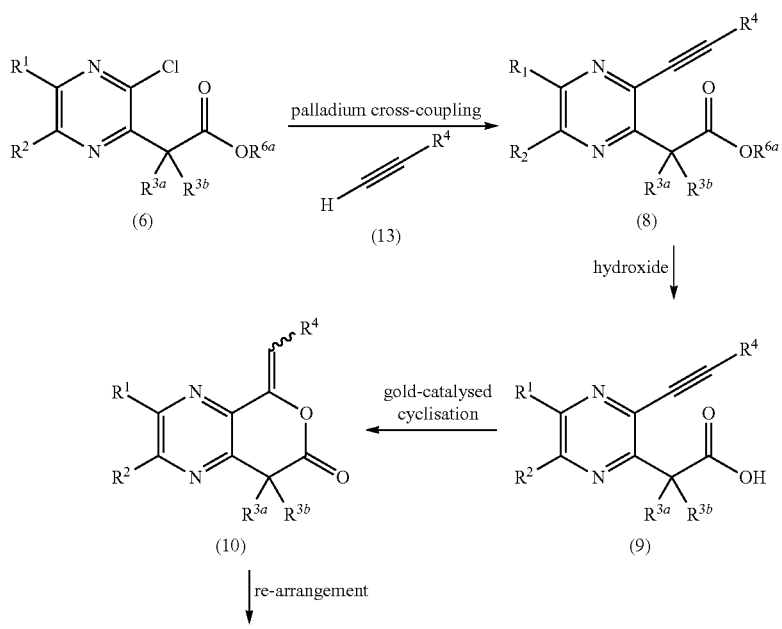

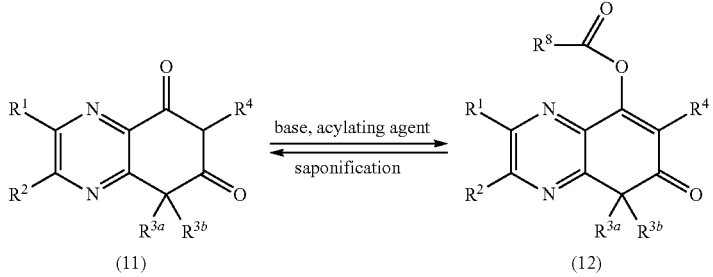

(11) → base, acylating agent / saponification → (12)

7. A pyranopyrazinone of formula (10) where $R^1$, $R^2$, $R^{3a}$, $R^{3b}$ and $R^4$ are as defined for a compound of formula (I) can be prepared by reacting an acid of formula (9), wherein $R^1$, $R^2$, $R^{3a}$, $R^{3b}$ and $R^4$ are as defined for a compound of formula (I), with a gold-based catalyst, preferably a gold(I) salt such as gold(I) chloride triphenylphosphine [AuCl(PPh$_3$)], preferably also in the presence of a silver-based catalyst (preferably a silver(I) salt such as silver(I) tetrafluoroborate or silver(I) trifluoromethanesulfonate), in an organic solvent, such as carbon tetrachloride, chloroform or dichloromethane. Suitably, the reaction temperature is 15 to 90° C. (e.g. 40 to 70° C., such as about 50-60° C.) and/or the reflux temperature of the organic solvent used.

8. A quinoxaline dione of formula (11) where $R^1$, $R^2$, $R^{3a}$, $R^{3b}$ and $R^4$ are as defined for a compound of formula (I) can be prepared by reacting a pyranopyrazinone of formula (10) where $R^1$, $R^2$, $R^{3a}$, $R^{3b}$ and $R^4$ are as defined for a compound of formula (I) in the presence of a base, preferably a tertiary amine base such as triethylamine or N,N-diisopropylethylamine, and a cyanide (CN$^-$) source, such as acetone cyanohydrin (Me$_2$C(OH)—CN), in a non-aqueous (e.g. anhydrous) organic solvent, such as acetonitrile. Molecular sieves can optionally be used in the reaction to remove water. Suitably, the reaction temperature is 0 to 30° C., such as room temperature which is usually ca. 18-25° C.

9. A quinoxalinyl ester of formula (12) where $R^1$, $R^2$, $R^{3a}$, $R^{3b}$ and $R^4$ are as defined for a compound of formula (I) can be prepared by reacting a quinoxaline dione of formula (11) where $R^1$, $R^2$, $R^{3a}$, $R^{3b}$ and $R^4$ are as defined for a compound of formula (I), optionally in unpurified form, with a suitable acid chloride, such as isobutryl chloride (isopropyl-C(O)—Cl, for when $R^8$ is isopropyl), in the presence of a base, such as pyridine or a tertiary amine base such as triethylamine or N,N-diisopropylethylamine, in a non-aqueous (e.g. anhydrous) organic solvent, such as dichloromethane. Suitably, the reaction temperature is 0 to 30° C., such as room temperature which is usually ca. 18-25° C. The prepared quinoxalinyl ester of formula (12) can then preferably be purified.

10. A quinoxaline dione of formula (11) where $R^1$, $R^2$, $R^{3a}$, $R^{3b}$ and $R^4$ are as defined for a compound of formula (I) can be prepared by reacting a quinoxalinyl ester of formula (12) where $R^1$, $R^2$, $R^{3a}$, $R^{3b}$ and $R^4$ are as defined for a compound of formula (I) with an aqueous solution of a hydroxide salt, such as aqueous lithium hydroxide, in a solvent such as ethanol and/or methanol. Suitably, the reaction temperature is 0 to 30° C., such as room temperature which is usually ca. 18-25° C. Step 10 can optionally be used, after purification of a quinoxalinyl ester of formula (12), to prepare purified quinoxaline dione of formula (11).

Herbicidal Compositions, Methods of Use, and Mixtures

The compounds of formula (I) according to the invention can be used as herbicides in unmodified form, as obtained in the synthesis, but they are generally formulated into herbicidal compositions in various ways my mixing with various substances (e.g. inert (i.e. substantially non-herbicidal) substances), such as carriers, solvents, adjuvants and/or surface-active substances.

The present invention therefore also provides a herbicidal composition (e.g. liquid herbicidal composition) which comprises a compound of formula (I) (e.g. a herbicidally effective amount thereof), and preferably also a carrier (e.g. liquid or solid carrier) and/or one or more solvents; and optionally also an adjuvant and/or a surface-active substance.

The herbicidal compositions (e.g. formulations) of the invention disclosed can be in various physical forms, for example in the form of dusting powders, gels, wettable powders, water-dispersible granules, water-dispersible tablets, effervescent pellets, emulsifiable concentrates, microemulsifiable concentrates, oil-in-water emulsions, oil-flowables, aqueous dispersions, oily dispersions, suspo-emulsions, capsule suspensions, emulsifiable granules, soluble liquids, water-soluble concentrates (with water or a water-miscible organic solvent as carrier), impregnated polymer films or in other forms known e.g. from the Manual on Development and Use of FAO Specifications for Plant Protection Products, 5th Edition, 1999. The herbicidal compositions (e.g. formulations) can either be used directly or they are diluted prior to use. The dilutions can be made, for example, with water, liquid fertilizers, micronutrients, biological organisms, oil or solvents.

The herbicidal compositions (e.g. formulations) can be prepared for example, by mixing the active ingredient with the formulation adjuvants in order to obtain compositions in the form of finely divided solids, granules, solutions, dispersions or emulsions. The active ingredients can also be formulated with other adjuvants, such as finely divided solids, mineral oils, oils of vegetable or animal origin, modified oils of vegetable or animal origin, organic solvents, water, surface-active substances or combinations thereof. The active ingredients can also be contained in very fine micro-capsules consisting of a polymer. Microcapsules contain the active ingredients in a porous carrier. This enables the active ingredients to be released into the environment in controlled amounts (e.g. slow-release). Microcapsules usually have a diameter of from 0.1 to 500 microns. They contain active ingredients in an amount of about from 25 to 95% by weight of the capsule weight. The active ingredients can be in the form of a monolithic solid, in the form of fine particles in solid or liquid dispersion or in the form of a suitable solution. The encapsulating membranes comprise, for example, natural or synthetic rubbers, cellulose, styrene/butadiene copolymers, polyacrylonitrile, polyacrylate, polyesters, polyamides, polyureas, polyurethane or chemically modified polymers and starch xanthates or other polymers that are known to the person skilled in the art in this connection.

Alternatively, very fine microcapsules can be formed in which the active ingredient is contained in the form of finely divided particles in a solid matrix of base substance, but the microcapsules are not themselves encapsulated.

The inert substances that are suitable for the preparation of the compositions according to the invention are known per se.

As liquid carriers there may be used: water, toluene, xylene, petroleum ether, vegetable oils, acetone, methyl ethyl ketone, cyclohexanone, acid anhydrides, acetonitrile, acetophenone, amyl acetate, 2-butanone, butylene carbonate, chlorobenzene, cyclohexane, cyclohexanol, alkyl esters of acetic acid, diacetone alcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethylformamide, dimethyl sulfoxide, 1,4-dioxane, dipropylene glycol, dipropylene glycol methyl ether, dipropylene glycol dibenzoate, diproxitol, alkylpyrrolidone, ethyl acetate, 2-ethylhexanol, ethylene carbonate, 1,1,1-trichloroethane, 2-heptanone, alpha-pinene, d-limonene, ethyl lactate, ethylene glycol, ethylene glycol butyl ether, ethylene glycol methyl ether, gamma-butyrolactone, glycerol, glycerol acetate, glycerol diacetate, glycerol triacetate, hexadecane, hexylene glycol, isoamyl acetate, isobornyl acetate, isooctane, isophorone, isopropylbenzene, isopropyl myristate, lactic acid, laurylamine, mesityl oxide, methoxypropanol, methyl isoamyl ketone, methyl isobutyl ketone, methyl laurate, methyl octanoate, methyl oleate, methylene chloride, m-xylene, n-hexane, n-octylamine, octadecanoic acid, octylamine acetate, oleic acid, oleylamine, o-xylene, phenol, polyethylene glycol (PEG400), propionic acid, propyl lactate, propylene carbonate, propylene glycol, propylene glycol methyl ether, p-xylene, toluene, triethyl phosphate, triethylene glycol, xylenesulfonic acid, paraffin, mineral oil, trichloroethylene, perchloroethylene, ethyl acetate, amyl acetate, butyl acetate, propylene glycol methyl ether, diethylene glycol methyl ether, methanol, ethanol, isopropanol, and alcohols of higher molecular weight, such as amyl alcohol, tetrahydrofurfuryl alcohol, hexanol, octanol, ethylene glycol, propylene glycol, glycerol, N-methyl-2-pyrrolidone and the like. Water is generally the liquid carrier of choice for diluting the concentrates.

Suitable solid carriers are, for example, talc, titanium dioxide, pyrophillite clay, silica, attapulgite clay, kieselguhr, limestone, calcium carbonate, bentonite, calcium montmorillonite, cottonseed husks, wheat flour, soybean flour, pumice, wood flour, ground walnut shells, lignin and similar substances, as described, for example, in CFR 180.1001. (c) & (d).

A large number of surface-active substances can advantageously be used in both solid and liquid formulations, especially in those formulations which can be diluted with a carrier prior to use. Surface-active substances may be anionic, cationic, non-ionic or polymeric and they can be used as emulsifiers, wetting agents or suspending agents or for other purposes. Typical surface-active substances include, for example, salts of alkyl sulfates, such as diethanolammonium lauryl sulfate; salts of alkylarylsulfonates, such as calcium dodecylbenzenesulfonate; alkylphenol/alkylene oxide addition products, such as nonylphenol ethoxylate; alcohol/alkylene oxide addition products, such as tridecylalcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryltrimethylammonium chloride, polyethylene glycol esters of fatty acids, such as polyethylene glycol stearate; block copolymers of ethylene oxide and propylene oxide; and salts of mono- and di-alkylphosphate esters; and also further substances described e.g. in "McCutcheon's Detergents and Emulsifiers Annual" MC Publishing Corp., Ridgewood N.J., 1981.

Further inert substances that can typically be used in herbicidal compositions (e.g. formulations) include crystallisation inhibitors, viscosity modifiers, suspending agents, dyes, anti-oxidants, foaming agents, light absorbers, mixing auxiliaries, antifoams, complexing agents, neutralizing or pH-modifying substances and buffers, corrosion inhibitors, fragrances, wetting agents, take-up enhancers, micronutrients, plasticisers, glidants, lubricants, dispersants, thickeners, antifreezes, microbicides, and also liquid and solid fertilizers.

The compositions according to the invention can additionally include an additive comprising an oil of vegetable or animal origin, a mineral oil, alkyl esters of such oils or mixtures of such oils and oil derivatives. The amount of oil additive in the composition according to the invention is generally from 0.01 to 10%, based on the spray mixture. For example, the oil additive can be added to the spray tank in the desired concentration after the spray mixture has been prepared. Preferred oil additives comprise mineral oils or an oil of vegetable origin, for example rapeseed oil, olive oil or sunflower oil, emulsified vegetable oil, such as AMIGO® (Rhône-Poulenc Canada Inc.), alkyl esters of oils of vegetable origin, for example the methyl derivatives, or an oil of animal origin, such as fish oil or beef tallow. A preferred additive contains, for example, as active components essentially 80% by weight alkyl esters of fish oils and 15% by weight methylated rapeseed oil, and also 5% by weight of customary emulsifiers and pH modifiers. Especially preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid, being of importance. Those esters are known as methyl laurate (CAS-111-82-0), methyl palmitate (CAS-112-39-0) and methyl oleate (CAS-112-62-9). A preferred fatty acid methyl ester derivative is Emery® 2230 and 2231 (Cognis GmbH). Those and other oil derivatives are also known from the Compendium of Herbicide Adjuvants, 5th Edition, Southern Illinois University, 2000.

The application and action of the oil additives can be further improved by combination with surface-active substances, such as non-ionic, anionic or cationic surfactants. Examples of suitable anionic, non-ionic and cationic surfactants are listed on pages 7 and 8 of WO 97/34485. Preferred surface-active substances are anionic surfactants of the dodecylbenzylsulfonate type, especially the calcium salts thereof, and also non-ionic surfactants of the fatty alcohol ethoxylate type. Special preference is given to ethoxylated $C_{12}$-$C_{22}$ fatty alcohols having a degree of ethoxylation of from 5 to 40. Examples of commercially available surfactants are the Genapol types (Clariant AG). Also preferred are silicone surfactants, especially polyalkyl-oxide-modified heptamethyltriloxanes which are commercially available e.g. as Silwet L-77®, and also perfluorinated surfactants. The concentration of the surface-active substances in relation to the total additive is generally from 1 to 30% by weight. Examples of oil additives consisting of mixtures of oil or mineral oils or derivatives thereof with surfactants are Edenor ME SU®, Turbocharge® (Syngenta AG, CH) or ActipronC (BP Oil UK Limited, GB).

If desired, it is also possible for the mentioned surface-active substances to be used in the formulations on their own, that is to say without oil additives.

Furthermore, the addition of an organic solvent to the oil additive/surfactant mixture may contribute to an additional enhancement of action. Suitable solvents are, for example, Solvesso® (ESSO) or Aromatic Solvent® (Exxon Corporation). The concentration of such solvents can be from 10 to 80% by weight of the total weight. Oil additives that are present in admixture with solvents are described, for example, in U.S. Pat. No. 4,834,908. A commercially available oil additive disclosed therein is known by the name MERGE® (BASF Corporation). A further oil additive that is preferred according to the invention is SCORE® (Syngenta Crop Protection Canada).

In addition to the oil additives listed above, for the purpose of enhancing the action of the compositions according to the invention it is also possible for formulations of alkylpyrrolidones (e.g. Agrimax®) to be added to the spray mixture. Formulations of synthetic lattices, e.g. polyacrylamide, polyvinyl compounds or poly-1-p-menthene (e.g. Bond®, Courier® or Emerald®) may also be used. It is also possible for solutions that contain propionic acid, for example Eurogkem Pen-e-trate®, to be added to the spray mixture as action-enhancing agent.

The herbicidal compositions generally comprise from 0.1 to 99% by weight, especially from 0.1 to 95% by weight, compounds of formula (I) and from 1 to 99.9% by weight of a formulation adjuvant which preferably includes from 0 to 25% by weight of a surface-active substance. Whereas commercial products will preferably be formulated as concentrates, the end user will normally employ dilute formulations.

Preferred formulations have especially the following compositions (%=percent by weight):

| Emulsifiable concentrates: | |
|---|---|
| active ingredient: | 1 to 95%, preferably 60 to 90% |
| surface-active agent: | 1 to 30%, preferably 5 to 20% |
| liquid carrier: | 1 to 80%, preferably 1 to 35% |
| Dusts: | |
| active ingredient: | 0.1 to 10%, preferably 0.1 to 5% |
| solid carrier: | 99.9 to 90%, preferably 99.9 to 99% |
| Suspension concentrates: | |
| active ingredient: | 5 to 75%, preferably 10 to 50% |
| water: | 94 to 24%, preferably 88 to 30% |
| surface-active agent: | 1 to 40%, preferably 2 to 30% |
| Wettable powders: | |
| active ingredient: | 0.5 to 90%, preferably 1 to 80% |
| surface-active agent: | 0.5 to 20%, preferably 1 to 15% |
| solid carrier: | 5 to 95%, preferably 15 to 90% |
| Granules: | |
| active ingredient: | 0.1 to 30%, preferably 0.1 to 15% |
| solid carrier: | 99.5 to 70%, preferably 97 to 85% |

The following formulation examples further illustrate, but do not limit, the invention.

Formulation Examples for Herbicides of Formula (I) (%=Percent by Weight)

| F1. Emulsifiable concentrates | a) | b) | c) | d) |
|---|---|---|---|---|
| active ingredient | 5% | 10% | 25% | 50% |
| calcium dodecylbenzenesulfonate | 6% | 8% | 6% | 8% |
| castor oil polyglycol ether (36 mol of ethylene oxide) | 4% | — | 4% | 4% |
| octylphenol polyglycol ether (7-8 mol of ethylene oxide) | — | 4% | — | 2% |
| NMP | — | — | 10% | 20% |
| arom. hydrocarbon mixture $C_9$-$C_{12}$ | 85% | 78% | 55% | 16% |

Emulsions of any desired concentration can be obtained from such concentrates by dilution with water.

| F2. Solutions | a) | b) | c) | d) |
|---|---|---|---|---|
| active ingredient | 5% | 10% | 50% | 90% |
| 1-methoxy-3-(3-methoxy-propoxy)-propane | — | 20% | 20% | — |
| polyethylene glycol MW 400 | 20% | 10% | — | — |
| NMP | — | — | 30% | 10% |
| arom. hydrocarbon mixture $C_9$-$C_{12}$ | 75% | 60% | — | — |

The solutions are suitable for use in the form of microdrops.

| F3. Wettable powders | a) | b) | c) | d) |
|---|---|---|---|---|
| active ingredient | 5% | 25% | 50% | 80% |
| sodium lignosulfonate | 4% | — | 3% | — |
| sodium lauryl sulfate | 2% | 3% | — | 4% |
| sodium diisobutylnaphthalenesulfonate | — | 6% | 5% | 6% |
| octylphenol polyglycol ether (7-8 mol of ethylene oxide) | — | 1% | 2% | — |
| highly dispersed silicic acid | 1% | 3% | 5% | 10% |
| kaolin | 88% | 62% | 35% | — |

The active ingredient is mixed thoroughly with the adjuvants and the mixture is thoroughly ground in a suitable mill, affording wettable powders which can be diluted with water to give suspensions of any desired concentration.

| F4. Coated granules | a) | b) | c) |
|---|---|---|---|
| active ingredient | 0.1% | 5% | 15% |
| highly dispersed silicic acid | 0.9% | 2% | 2% |
| [inorganic carrier (diameter 0.1-1 mm) for example $CaCO_3$ or $SiO_2$] | 99.0% | 93% | 83% |

The active ingredient is dissolved in methylene chloride and applied to the carrier by spraying, and the solvent is then evaporated off in vacuo.

| F5. Coated granules | a) | b) | c) |
|---|---|---|---|
| active ingredient | 0.1% | 5% | 15% |
| polyethylene glycol MW 200 | 1.0% | 2% | 3% |
| highly dispersed silicic acid | 0.9% | 1% | 2% |
| [inorganic carrier (diameter 0.1-1 mm) for example $CaCO_3$ or $SiO_2$] | 98.0% | 92% | 80% |

The finely ground active ingredient is uniformly applied, in a mixer, to the carrier moistened with polyethylene glycol. Non-dusty coated granules are obtained in this manner.

| F6. Extruder granules | a) | b) | c) | d) |
|---|---|---|---|---|
| active ingredient | 0.1% | 3% | 5% | 15% |
| sodium lignosulfonate | 1.5% | 2% | 3% | 4% |
| carboxymethylcellulose | 1.4% | 2% | 2% | 2% |
| kaolin | 97.0% | 93% | 90% | 79% |

The active ingredient is mixed and ground with the adjuvants, and the mixture is moistened with water. The mixture is extruded and then dried in a stream of air.

| F7. Dusts | a) | b) | c) |
|---|---|---|---|
| active ingredient | 0.1% | 1% | 5% |
| talcum | 39.9% | 49% | 35% |
| kaolin | 60.0% | 50% | 60% |

Ready-to-use dusts are obtained by mixing the active ingredient with the carriers and grinding the mixture in a suitable mill.

| F8. Suspension concentrates | a) | b) | c) | d) |
|---|---|---|---|---|
| active ingredient | 3% | 10% | 25% | 50% |
| ethylene glycol | 5% | 5% | 5% | 5% |
| nonylphenol polyglycol ether (15 mol of ethylene oxide) | — | 1% | 2% | — |
| sodium lignosulfonate | 3% | 3% | 4% | 5% |
| carboxymethylcellulose | 1% | 1% | 1% | 1% |
| 37% aqueous formaldehyde solution | 0.2% | 0.2% | 0.2% | 0.2% |
| silicone oil emulsion | 0.8% | 0.8% | 0.8% | 0.8% |
| water | 87% | 79% | 62% | 38% |

The finely ground active ingredient is intimately mixed with the adjuvants, giving a suspension concentrate from which suspensions of any desired concentration can be obtained by dilution with water.

Methods of Use

The present invention further relates to a method of controlling a plant (e.g. a grass and/or a weed) which comprises applying to the plant (e.g. to a crop of useful plants) or to the locus thereof a herbicidally effective amount of a compound of formula (I).

The invention also relates to a method of inhibiting plant growth (e.g. in a grass and/or a weed) which comprises applying to the plant (e.g. to a crop of useful plants) or to the locus thereof a herbicidally effective amount of a compound of formula (I).

The invention also relates to a method of selectively controlling a grass and/or a weed in a crop of a useful plants which comprises applying to the useful plants or locus thereof or to the area of cultivation a herbicidally effective amount of a compound of formula (I).

A compound of formula (I), and/or a herbicidal composition and/or mixture containing the same, may also be applied to turf, pasture, rangeland, a right of way etc. In particular they may be used on a golf-course, a lawn, a park, a sportsfield, a race-course or similar.

The term "herbicide" as used herein means a compound that controls or modifies the growth of plants. The term "herbicidally effective amount" means the quantity of such a compound or combination of such compounds that is capable of producing a controlling or modifying effect on the growth of plants. Controlling or modifying effects include all deviation from natural development, for example: killing, retardation, leaf burn, albinism, dwarfing or similar. The term "plant" or "plants" refers to all physical parts of a plant, such as seeds, seedlings, saplings, roots, tubers, stems, stalks, foliage, or fruits. The term "locus" is intended to include soil, seeds, or seedlings, as well as established vegetation.

The crop of useful plants, e.g. in or to which a compound, composition, mixture or method according to the invention can be used or applied, can for example be a perennial crop, such as citrus fruit, grapevines, nuts, oil palms, olives, pome fruit, stone fruit or rubber; or an annual arable crop, such as a cereal (e.g. wheat, barley, rye, or triticale, etc.), cotton, oilseed rape, maize (corn), rice, soybean, sugarbeet, sugarcane, sunflowers, an ornamental or a vegetable; especially a cereal, maize or soybean.

The grass and/or weed to be controlled can be monocotyledonous and/or dicotyledonous species. The grass and/or weed to be controlled can be a monocotyledonous species, for example *Agrostis*, *Alopecurus* (e.g. *Alopecurus myosuroides*), *Avena* (e.g. *Avena fatua*), *Bromus*, *Cyperus*, *Digitaria* (e.g. *Digitaria sanguinalis*), *Echinochloa* (e.g. *Echinochloa crus-galli*), *Lolium* (e.g. *Lolium perenne*), *Monochoria*, *Rottboellia*, *Sagittaria*, *Scirpus*, *Setaria* (e.g. *Setaria faberi*), or *Sorghum*; or more preferably is a dicotyledonous species, for example *Abutilon* (e.g. *Abutilon theophrasti*), *Amaranthus* (e.g. *Amaranthus retroflexus*), *Bidens* (e.g. *Bidens pilosa*), *Chenopodium* (e.g. *Chenopodium album*), *Chrysanthemum*, *Euphorbia* (e.g. *Euphorbia hetrophylla*), *Galium* (e.g. *Galium aparine*), *Ipomoea* (e.g. *Ipomea hederaceae*), *Nasturtium*, *Sida* (e.g. *Sida spinosa*), *Sinapis* (e.g. *Sinapis arvensis*), *Solanum* (e.g. *Solanum nigrum*), *Stellaria* (e.g. *Stellaria media*), *Veronica* (e.g. *Veronica persica* or *Veronica hederifolia*), *Viola* (e.g. *Viola arvensis*) or *Xanthium*.

Crops are to be understood as also including those crops which have been rendered tolerant to herbicides or classes of herbicides (e.g. auxins or ALS-, GS-, EPSPS-, PPO- and HPPD-inhibitors) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®.

Crops are also to be understood as including those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). The Bt toxin is a protein that is formed naturally by *Bacillus thuringiensis* soil bacteria. Examples of toxins, or transgenic plants able to synthesize such toxins, are described in EP-A-451 878, EP-A-374 753, WO 93/07278, WO 95/34656, WO 03/052073 and EP-A-427 529. Examples of transgenic plants comprising one or more genes that code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®. Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crops are also to be understood as including those which are obtained by conventional methods of breeding or genetic engineering and contain so-called output traits (e.g. improved storage stability, improved stress (e.g. drought) resistance, higher nutritional value and/or improved flavor).

Areas under cultivation include land on which the crop plants are already growing and land intended for cultivation with those crop plants. The compounds of the invention can be applied before weeds emerge (pre-emergence application) or after weeds emerge (post-emergence application), and are particularly effective when applied post-emergence.

The rates of application of compounds of formula (I) (e.g. rate of application to a crop of useful plants, or to a grass and/or a weed, or to the locus thereof, or to the area of cultivation) may vary within wide limits and may depend on the nature of the soil, the method of application (pre- or post-emergence; seed dressing; application to the seed furrow; no tillage application etc., whether the compound of formula (I) is applied as a mixture with a further herbicide), the crop plant, the grass and/or weed to be controlled, the prevailing climatic conditions, and/or other factors governed by the method of application, the time of application and the target crop. The compounds of formula (I) according to the invention, are generally applied (e.g. to a crop of useful plants, or to a grass and/or a weed, or to the locus thereof, or to the area of cultivation) at a rate of from 10 to 2000 g/ha, in particular from 50 to 1000 g/ha, e.g. whether applied as a sole herbicide or as a mixture containing a further herbicide.

Mixtures/Combinations

The compounds of formula (I) according to the invention can also be used in combination with one or more further herbicides. Some of the combinations/mixtures may lead to synergistic effects and/or may confer one or more technical effects and/or advantages.

The invention therefore provides a mixture (e.g. herbicidal composition, e.g. liquid or solid), which comprises a herbicidally effective amount of a compound of formula (I), and a further herbicide as a mixture partner for the compound of formula (I).

In particular, the following mixtures of the compound of formula (I) are important, where numbers given in brackets after compound names are often the corresponding reference numbers given in The Pesticide Manual, 13th Edition (BCPC), 2003:

Mixtures of a compound of formula (I) with a synthetic auxin (e.g. a compound of formula (I) with clopyralid (162); a compound of formula (I) with 2,4-D (211); a compound of formula (I) with dicamba (228); a compound of formula (I) with diphenamid (274); a compound of formula (I) with MCPA (499); a compound of formula (I) with quinclorac (712); a compound of formula (I) with aminopyralid (CAS RN 150114-71-9); a compound of formula (I) with 4-amino-3-chloro-6-(4-chloro-2-fluoro-3-methoxyphenyl)-2-pyridinecarboxylic acid (CAS RN 943832-60-8); or a compound of formula (I) with 4-amino-3-chloro-6-(4-chloro-2-fluoro-3-methoxyphenyl)-2-pyridinecarboxylic acid, methyl ester (CAS RN 943831-98-9)).

Mixtures of a compound of formula (I) with diflufenzopyr (252).

Mixtures of a compound of formula (I) with an acetanilide (e.g. a compound of formula (I) with acetochlor (5), a compound of formula (I) with dimethenamid (260), a compound of formula (I) with metolachlor (548), a compound of formula (I) with S-metolachlor (549), or a compound of formula (I) with pretilachlor (656)).

Mixtures of a compound of formula (I) with flamprop-M (355).

Mixtures of a compound of formula (I) with flufenacet (BAY FOE 5043) (369).

Mixtures of a compound of formula (I) with pyroxasulfone (CAS RN 447399-55-5).

Mixtures of a compound of formula (I) with an HPPD inhibitor (e.g. a compound of formula (I) with isoxaflutole (479), a compound of formula (I) with mesotrione (515), a compound of formula (I) with pyrasulfotole (CAS RN 365400-11-9), a compound of formula (I) with sulcotrione (747), a compound of formula (I) with tembotrione (CAS RN 335104-84-2), compound of formula (I) with topramezone (CAS RN 210631-68-8), a compound of formula (I) with 4-hydroxy-3-[[2-[(2-methoxyethoxy)methyl]-6-(trifluoromethyl)-3-pyridinyl]carbonyl]-bicyclo[3.2.1]oct-3-en-2-one (CAS RN 352010-68-a 5), or compound of formula (I) with 4-hydroxy-3-[[2-(3-methoxypropyl)-6-(difluoromethyl)-3-pyridinyl]carbonyl]-bicyclo[3.2.1]oct-3-en-2-one (CAS RN 894355-80-7)).

Mixtures of a compound of formula (I) with a triazine (e.g. a compound of formula (I) with atrazine (37); or a compound of formula (I) with terbuthylazine (775)).

Mixtures of a compound of formula (I) with a triazine and an HPPD inhibitor (e.g. a compound of formula (I) with triazine with isoxaflutole, a compound of formula (I) with triazine with mesotrione, a compound of formula (I) with triazine with pyrasulfotole, a compound of formula (I) with triazine with sulcotrione, a compound of formula (I) with triazine with tembotrione, a compound of formula (I) with triazine with topramezone, compound of formula (I) with triazine with 4-hydroxy-3-[[2-[(2-methoxyethoxy)methyl]-6-(trifluoromethyl)-3-pyridinyl]carbonyl]-bicyclo[3.2.1]oct-3-en-2-one, or a compound of formula (I) with triazine with 4-hydroxy-3-[[2-(3-methoxypropyl)-6-(difluoromethyl)-3-pyridinyl]carbonyl]-bicyclo[3.2.1]oct-3-en-2-one).

Mixtures of a compound of formula (I) with glyphosate (419).

Mixtures of a compound of formula (I) with glyphosate and an HPPD inhibitor (e.g. a compound of formula (I) with glyphosate with isoxaflutole, a compound of formula (I) with glyphosate with mesotrione, a compound of formula (I) with glyphosate with pyrasulfotole, a compound of formula (I) with glyphosate with sulcotrione, a compound of formula (I) with glyphosate with tembotrione, a compound of formula (I) with glyphosate with topramezone, a compound of formula (I) with glyphosate with 4-hydroxy-3-[[2-[(2-methoxyethoxy)methyl]-6-(trifluoromethyl)-3-pyridinyl]carbonyl]-bicyclo[3.2.1]oct-3-en-2-one, or a compound of formula (I) with glyphosate with 4-hydroxy-3-[[2-(3-methoxypropyl)-6-(difluoromethyl)-3-pyridinyl]carbonyl]-bicyclo[3.2.1]oct-3-en-2-one).

Mixtures of a compound of formula (I) with glufosinate-ammonium (418).

Mixtures of a compound of formula (I) with glufosinate-ammonium and an HPPD inhibitor (e.g. a compound of formula (I) with glufosinate-ammonium with isoxaflutole, a compound of formula (I) with glufosinate-ammonium with mesotrione, a compound of formula (I) with glufosinate-ammonium with pyrasulfotole, a compound of formula (I) with glufosinate-ammonium with sulcotrione, a compound of formula (I) with glufosinate-ammonium with tembotrione, a compound of formula (I) with glufosinate-ammonium with topramezone, a compound of formula (I) with glufosinate-ammonium with 4-hydroxy-3-[[2-[(2-methoxyethoxy)methyl]-6-(trifluoromethyl)-3-pyridinyl]carbonyl]-bicyclo[3.2.1]oct-3-en-2-one, or a compound of formula (I) with glufosinate-ammonium with 4-hydroxy-3-[[2-(3-methoxypropyl)-6-(difluoromethyl)-3-pyridinyl]carbonyl]-bicyclo[3.2.1]oct-3-en-2-one).

Mixtures of a compound of formula (I) with an ALS or an AHAS inhibitor (e.g. a compound of formula (I) with bensulfuron-methyl (64), a compound of formula (I) with chlorimuron-ethyl (135), compound of formula (I) with cloransulam-methyl (164), a compound of formula (I) with florasulam (359), a compound of formula (I) with flucarbazone-sodium (364), a compound of formula (I) with imazamox (451), a compound of formula (I) with imazapyr (453), a compound of formula (I) with imazethapyr (455), a compound of formula (I) with iodosulfuron-methyl-sodium (466), a compound of formula (I) with mesosulfuron-methyl (514), a compound of formula (I) with nicosulfuron (577), a compound of formula (I) with penoxsulam (622), a compound of formula (I) with pyroxsulam (triflosulam) (CAS RN 422556-08-9), a compound of formula (I) with thifensulfuron-methyl (thiameturon-methyl) (795), a compound of formula (I) with triasulfuron (817), a compound of formula (I) with tribenuron-methyl (822), a compound of formula (I) with trifloxysulfuron-sodium (833), a compound of formula (I) with thiencarbazone (4-[(4,5-dihydro-3-methoxy-4-methyl-5-oxo-1H-1,2,4-triazol-1-yl)carbonylsulfamoyl]-5-methylthiophene-3-carboxylic acid, BAY636)), or a compound of formula (I) with thiencarbazone-methyl (methyl 4-[(4,5-dihydro-3-methoxy-4-methyl-5-oxo-1H-1,2,4-triazol-1-yl)carbonylsulfamoyl]-5-methylthiophene-3-carboxylate, CAS RN 317815-83-1, BAY636-methyl)).

Mixtures of a compound of formula (I) with a PPO inhibitor (e.g. compound of formula (I) with acifluorfen-sodium (7), a compound of formula (I) with butafenacil (101), a compound of formula (I) with carfentrazone-ethyl (121), a compound of formula (I) with cinidon-ethyl (152), a compound of formula (I) with flumioxazin (376), a compound of formula (I) with fomesafen (401), a compound of formula (I) with lactofen (486), or a compound of formula (I) with [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester) (CAS RN 353292-31-6)).

Mixtures of a compound of formula (I) with an acetyl-CoA carboxylase inhibitor (ACCase inhibitor) (e.g. a compound of formula (I) with butroxydim (106), a compound of formula (I) with clethodim (155), a compound of formula (I) with clodinafop-propargyl (156), a compound of formula (I) with cycloxydim (190), a compound of formula (I) with cyhalofop-butyl (195), a compound of formula (I) with diclofop-methyl (238), a compound of formula (I) with fenoxaprop-P-ethyl (339), a compound of formula (I) with fluazifop-butyl (361), a compound of formula (I) with fluazifop-P-butyl (362), a compound of formula (I) with haloxyfop (427), a compound of formula (I) with haloxyfop-P (428), a compound of formula (I) with propaquizafop (670), a compound of formula (I) with quizalofop (717), a compound of formula (I) with quizalofop-P (718), compound of formula (I) with sethoxydim (726), a compound of formula (I) with tepraloxydim (771), a compound of formula (I) with tralkoxydim (811)), or a compound of formula (I) with pinoxaden (CAS RN 243973-20-8).

Mixtures of a compound of formula (I) with prosulfocarb (683), or a compound of formula (I) with tri-allate (816).

Mixtures of a compound of formula (I) with bromoxynil (95), a compound of formula (I) with chloridazon (134), a compound of formula (I) with chlorotoluron (143), a compound of formula (I) with diuron (281), or a compound of formula (I) with metribuzin (554).

Mixtures of a compound of formula (I) with clomazone (159), a compound of formula (I) with diflufenican (251), a compound of formula (I) with fluorochloridone (389), or a compound of formula (I) with flurtamone (392).

Mixtures of a compound of formula (I) with pendimethalin (621) or a compound of formula (I) with trifluralin (836).

Mixtures of a compound of formula (I) with difenzoquat metilsulfate (248).

Mixtures of a compound of formula (I) with diquat dibromide (276).

Mixtures of a compound of formula (I) with paraquat dichloride (614).

The mixing partners of the compound of formula (I) may also be in the form of esters or salts, as mentioned for example in The Pesticide Manual, 13th Edition (BCPC), 2003. The reference to glufosinate-ammonium also applies to glufosinate, the reference to cloransulam-methyl also applies to cloransulam, the reference to dimethenamid also applies to dimethenamid-P, the reference to flamprop-M also applies to flamprop, and the reference to pyrithiobac-sodium also applies to pyrithiobac, etc.

The mixing ratio of the compound of formula (I) to the mixing partner (e.g. further herbicide) is typically from 1:300 to 300:1 by weight or from 1:100 to 100:1 by weight; or preferably from 1:30 to 30:1 by weight.

The mixtures can advantageously be used in the above-mentioned formulations (in which case "active ingredient" relates to the respective mixture of compound of formula (I) with the mixing partner).

Additionally, one or more of the following further herbicides or plant growth regulators (typically plant growth inhibitors) can be used in combination with a compound of formula (I) according to the invention or in combination with a mixture as described above: aclonifen (8), acrolein (10), alachlor (14), alloxydim (18), ametryn (20), amicarbazone (21), amidosulfuron (22), aminocyclopyrachlor (CAS RN 858956-08-8), amitrole (aminotriazole) (25), ammonium sulfamate (26), anilofos (31), asulam (36), aviglycine (39), azafenidin (CAS RN 68049-83-2), azimsulfuron (43), BAS 800H (CAS RN 372137-35-4), beflubutamid (55), benazolin (57), bencarbazone (CAS RN 173980-17-1), benfluralin (59), benfuresate (61), bensulide (65), bentazone (67), benzfendizone (CAS RN 158755-95-4), benzobicyclon (69), benzofenap (70), bilanafos (bialaphos) (77), bispyribac-sodium (82), borax (86), bromacil (90), bromobutide (93), bromofenoxim (CAS RN 13181-17-4), butachlor (100), butamifos (102), butralin (105), butylate (108), cafenstrole (110), carbetamide (117), chlorbromuron (CAS RN 13360-45-7), chlorflurenol-methyl (133), chloroacetic acid (138), chlorpropham (144), chlorsulfuron (147), chlorthal-dimethyl (148), cinmethylin (153), cinosulfuron (154), clomeprop (160), cumyluron (180), cyanamide (182), cyanazine (183), cyclanilide (186), cycloate (187), cyclosulfamuron (189), daimuron (213), dalapon (214), dazomet (216), desmedipham (225), desmetryn (CAS RN 1014-69-3), dichlobenil (229), dichlorprop (234), dichlorprop-P (235), diclosulam (241), dimefuron (256), dimepiperate (257), dimethachlor (258), dimethametryn (259), dimethipin (261), dimethylarsinic acid (264), dinitramine (268), dinoterb (272), dipropetryn (CAS RN 4147-51-7), dithiopyr (280), DNOC (282), DSMA (CAS RN 144-21-8), endothal (295), EPTC (299), esprocarb (303), ethalfluralin (305), ethametsulfuron-methyl (306), ethephon (307), ethofumesate (311), ethoxyfen (CAS RN 188634-90-4), ethoxyfen-ethyl (CAS RN 131086-42-5), ethoxysulfuron (314), etobenzanid (318), fentrazamide (348), ferrous sulfate (353), flazasulfuron (356), fluazolate (isopropazol) (CAS RN 174514-07-9), flucetosulfuron (CAS RN 412928-75-7), fluchloralin (365), flufenpyr-ethyl (371), flumetralin (373), flumetsulam (374), flumiclorac-pentyl (375), flumipropyn (flumipropin) (CAS RN 84478-52-4), flumeturon (378), fluoroglycofen-ethyl (380), flupoxam (CAS RN 119126-15-7), flupropacil (CAS RN 120890-70-2), flupropanate (383), flupyrsulfuron-methyl-sodium (384), flurenol (387), fluridone (388), fluoroxypyr (390), fluthiacet-methyl (395), foramsulfuron (402), fosamine (406), halosulfuron-methyl (426), HC-252 (429), hexazinone (440), imazamethabenz-methyl (450), imazapic (452), imazaquin (454), imazosulfuron (456), indanofan (462), ioxynil (467), isoproturon (475), isouron (476), isoxaben (477), isoxachlortole (CAS RN 141112-06-3), isoxapyrifop (CAS RN 87757-18-4), karbutilate (482), lenacil (487), linuron (489), MCPA-thioethyl (500), MCPB (501), mecoprop (503), mecoprop-P (504), mefenacet (505), mefluidide (507), metam (519), metamifop (mefluoxafop) (520), metamitron (521), metazachlor (524), methabenzthiazuron (526), methazole (CAS RN 20354-26-1), methylarsonic acid (536), 1-methylcyclopropene (538), methyldymron (539), methyl isothiocyanate (543), metobenzuron (547), metobromuron (CAS RN 3060-89-7), metosulam (552), metoxuron (553), metsulfuron-methyl (555), MK-616 (559), molinate (560), monolinuron (562), MSMA (CAS RN 2163-80-6), naproanilide (571), napropamide (572), naptalam (573), neburon (574), nipyraclofen (CAS RN 99662-11-0), n-methyl-glyphosate, nonanoic acid (583), norflurazon (584), oleic acid (fatty acids) (593), orbencarb (595), orthosulfamuron (CAS RN 213464-77-8), oryzalin (597), oxadiargyl (599), oxadiazon (600), oxasulfuron (603), oxaziclomefone (604), oxyfluorfen (610), pebulate (617), pentachlorophenol (623), pentanochlor (624), pentoxazone (625), pethoxamid (627), petrolium oils (628), phenmedipham (629), picloram (645), picolinafen (646), piperophos (650), primisulfuron-methyl (657), prodiamine (661), profluazol (CAS RN 190314-43-3), profoxydim (663), prohexadione calcium (664), prometon (665), prometryn (666), propachlor (667), propanil (669), propazine (672), propham (674), propisochlor (667), propoxycarbazone-sodium (procarbazone-sodium) (679), propyzamide (681), prosulfuron (684), pyraclonil (pyrazogyl) (CAS RN 158353-15-2), pyraflufen-ethyl (691), pyrazolynate (692), pyrazosulfuron-ethyl (694), pyrazoxyfen (695), pyribenzoxim (697), pyributicarb (698), pyridafol (CAS RN 40020-01-7), pyridate (702), pyriftalid (704), pyriminobac-methyl (707), pyrimisulfan (CAS RN 221205-90-9), pyrithiobac-sodium (709), quinmerac (713), quinoclamine (714), rimsulfuron (721), sequestrene, siduron (727), simazine (730), simetryn (732), sodium chlorate (734), sulfentrazone (749), sulfometuron-methyl (751), sulfosate (CAS RN 81591-81-3), sulfosulfuron (752), sulfuric acid (755), tar oils (758), TCA-sodium (760), tebutam (CAS RN 35256-85-0), tebuthiuron (765), tefuryltrione (CAS RN 473278-76-1), terbacil (772), terbumeton (774), terbutryn (776), thenylchlor (789), thidiazimin (CAS RN 123249-43-4), thiazafluoron (CAS RN 25366-23-8), thiazopyr (793), thiobencarb (797), tiocarbazil (807), triaziflam (819), triclopyr (827), trietazine (831), triflusulfuron-methyl (837), trihydroxytriazine (CAS RN 108-80-5), trinexapac-ethyl (CAS RN 95266-40-3), tritosulfuron (843), N-[(1R,2S)-2,6-dimethyl-2,3-dihydro-1H-inden-1-yl]-6-(1-fluoroethyl)-1,3,5-triazine-2,4-diamine (CAS RN 950782-86-2), 1-(2-chloro-6-propylimidazo[1,2-b]pyridazin-3-ylsulfonyl)-3-(4,6-dimethoxypyrimidin-2-Aurea (CAS RN 570415-88-2), or 5-(2,6-difluoro-benzyloxymethyl)-5-methyl-3-(3-methylthiophen-2-yl)-4,5-dihydro-isoxazole (CAS RN 403640-27-7).

The mixing partners of the compound of formula (I) may also be in the form of esters or salts, as mentioned e.g. in The Pesticide Manual, 13th Edition (BCPC), 2003. The reference to acifluorfen-sodium also applies to acifluorfen, and the reference to bensulfuron-methyl also applies to bensulfuron, etc.

The mixing ratio of the compound of formula (I) to the mixing partner (e.g. further herbicide) is typically from 1:300 to 300:1 by weight or from 1:100 to 100:1 by weight; or preferably from 1:30 to 30:1 by weight.

The mixtures can advantageously be used in the above-mentioned formulations (in which case "active ingredient" relates to the respective mixture of compound of formula (I) with the mixing partner).

The compounds of formula (I) according to the invention can also be used in combination with one or more safeners. Likewise, mixtures of a compound of formula (I) according to the invention with one or more further herbicides can also be used in combination with one or more safeners. The term "safener" as used herein means a chemical that when used in combination with a herbicide reduces the undesirable effects of the herbicide on non-target plants, for example, typically a safener protects crop plants from injury by herbicides, or minimizes such injury, but does not prevent the herbicide from killing or inhibiting the growth of weeds.

The invention therefore provides a mixture (e.g. herbicidal composition, e.g. liquid or solid), which comprises a herbicidally effective amount of a compound of formula (I) and a safener.

The invention also provides a mixture (e.g. herbicidal composition, e.g. liquid or solid), which comprises a herbicidally effective amount of a compound of formula (I), a further herbicide as a mixture partner for the compound of formula (I), and a safener.

The safener can be AD-67 (11), benoxacor (63), cloquintocet-mexyl (163), cyometrinil (CAS RN 78370-21-5), cyprosulfamide (CAS RN 221667-31-8), dichlormid (231), dicyclonon (CAS RN 79260-71-2), fenchlorazole-ethyl (331), fenclorim (332), flurazole (386), fluxofenim (399), furilazole (413) or the corresponding R isomer thereof, isoxadifen-ethyl (478), mefenpyr-diethyl (506), 2-methoxy-N-[[4-[[(methylamino)carbonyl]amino]phenyl]sulfonyl]-benzamide (CAS RN 129531-12-0), naphthalic anhydride (CAS RN 81-84-5), N-(2-methoxybenzoyl)-4-[(methylaminocarbonyl)amino]benzenesulfonamide, or oxabetrinil (598).

In one particular embodiment, the safener is benoxacor, cloquintocet-mexyl, mefenpyr-diethyl, cyprosulfamide or N-(2-methoxybenzoyl)-4-[(methylaminocarbonyl)amino] benzenesulfonamide.

The mixture with the safener can be applied to a crop of useful plants, for example a perennial crop, such as citrus fruit, grapevines, nuts, oil palms, olives, pome fruit, stone fruit or rubber; or an annual arable crop, such as a cereal (e.g. wheat, barley, rye, or triticale, etc.), cotton, oilseed rape, maize (corn), rice, soybean, sugarbeet, sugarcane, sunflowers, an ornamental or a vegetable.

The safeners of the compound of formula (I) may also be in the form of esters or salts, as mentioned e.g. in The Pesticide Manual, 13th Edition (BCPC), 2003. The reference to cloquintocet-mexyl also applies to cloquintocet, the reference to mefenpyr-diethyl also applies to mefenpyr, and the reference to fenchlorazole-ethyl also applies to fenchlorazole, etc.

Preferably, in the mixture, the ratio of the compound of formula (I) to the safener is from 100:1 to 1:10 by weight, especially from 20:1 to 1:1 by weight.

The mixtures can advantageously be used in the above-mentioned formulations (in which case "active ingredient" relates to the respective mixture of compound of formula (I) with the safener). It is possible that the safener and a compound of formula (I) and one or more additional herbicide(s), if any, are applied simultaneously. For example, the safener, a compound of formula (I) and one or more additional herbicide(s), if any, might be applied to the locus pre-emergence or might be applied to the crop post-emergence. It is also possible that the safener and a compound of formula (I) and one or more additional herbicide(s), if any, are applied sequentially. For example, the safener might be applied before sowing the seeds as a seed treatment and a compound of formula (I) and one or more additional herbicides, if any, might be applied to the locus pre-emergence or might be applied to the crop post-emergence.

Preferred mixtures of a compound of formula (I) with further herbicides and safeners include:

Mixtures of a compound of formula (I) with S-metolachlor and a safener, particularly benoxacor.

Mixtures of a compound of formula (I) with S-metolachlor and mesotrione and a safener, particularly benoxacor.

Mixtures of a compound of formula (I) with isoxaflutole and a safener.

Mixtures of a compound of formula (I) with mesotrione and a safener, particularly benoxacor.

Mixtures of a compound of formula (I) with sulcotrione and a safener.

Mixtures of a compound of formula (I) with a triazine and a safener.

Mixtures of a compound of formula (I) with a triazine and isoxaflutole and a safener.

Mixtures of a compound of formula (I) with a triazine and mesotrione and a safener.

Mixtures of a compound of formula (I) with a triazine and sulcotrione and a safener.

Mixtures of a compound of formula (I) with glyphosate and a safener.

Mixtures of a compound of formula (I) with glyphosate and isoxaflutole and a safener.

Mixtures of a compound of formula (I) with glyphosate and mesotrione and a safener.

Mixtures of a compound of formula (I) with glyphosate and sulcotrione and a safener.

Mixtures of a compound of formula (I) with glufosinate-ammonium and a safener.

Mixtures of a compound of formula (I) with glufosinate-ammonium and isoxaflutole and asafener.

Mixtures of a compound of formula (I) with glufosinate-ammonium and mesotrione and a safener.

Mixtures of a compound of formula (I) with glufosinate-ammonium and sulcotrione and a safener.

Mixtures of a compound of formula (I) with florasulam and a safener, particularly cloquintocet-mexyl.

Mixtures of a compound of formula (I) with clodinafop-propargyl and a safener, particularly cloquintocet-mexyl.

Mixtures of a compound of formula (I) with pinoxaden and a safener, particularly cloquintocet-mexyl.

Mixtures of a compound of formula (I) with bromoxynil and a safener, particularly cloquintocet-mexyl.

The following Examples further illustrate, but do not limit, the invention.

EXAMPLES

Abbreviations
DMF dimethylformamide
LHMDS lithium hexamethyldisilazide
NMR nuclear magnetic resonance
LCMS liquid chromatography—mass spectrometry
GCMS gas chromatography—mass spectrometry
RT (in the context of LCMS or GCMS) retention time
RT (in the context of temperature) room temperature (ambient temperature), which is usually about 18-25° C.

Example 1

Reactions Covered by Reaction Scheme 1

Example 1.1

Preparation of 2-(3-Chloro-pyrazin-2-yl)-malonic acid diethyl ester

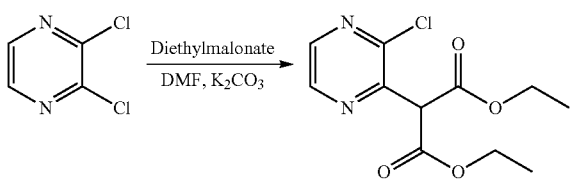 [SMILES: Clc1nccnc1Cl ; CCOC(=O)C(C(=O)OCC)c1nccnc1Cl]

To a solution of 2,3-dichloro-pyrazine (10 g) (commercially available) and N,N-dimethylformamide ("DMF") (80 ml) was added diethylmalonate (26.87 g) and potassium carbonate (23.19 g). The reaction mixture was heated to 110° C. for 8 hours. The reaction mixture was cooled to ambient temperature, filtered and the filtrate concentrated. The residue was purified by chromatography on silica gel (eluent 5-95% ethyl acetate in isohexane) to give 2-(3-Chloro-pyrazin-2-yl)-malonic acid diethyl ester (12.93 g). $^1$H-NMR (400 MHz, CDCl$_3$): 8.50 (s, 1H), 8.40 (s, 1H), 5.20 (s, 1H), 4.30 (q, 4H), 1.30 (t, 6H) ppm.

Example 1.2

Preparation of (3-Chloro-pyrazin-2-yl)-acetic acid

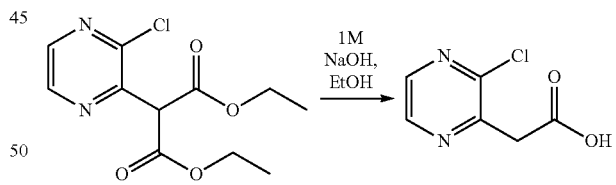

To a solution of 2-(3-chloro-pyrazin-2-yl)-malonic acid diethyl ester (10.0 g) in ethanol (100 ml) was added 2M sodium hydroxide (100 ml) and the reaction mixture heated to 60° C. for 4 hours. The reaction mixture was cooled to ambient temperature then poured onto water and 1M hydrochloric acid followed by extraction with ethyl acetate (3×). The combined organic layers were dried (magnesium sulfate), filtered and the filtrate concentrated to give the crude title compound as a yellow solid. The solid was slurried with diethylether to give (3-chloro-pyrazin-2-yl)-acetic acid (4.35 g). MH$^+$=173, RT=0.72 min (Method A).

Example 1.3

Preparation of (3-Chloro-pyrazin-2-yl)-acetic acid ethyl ester

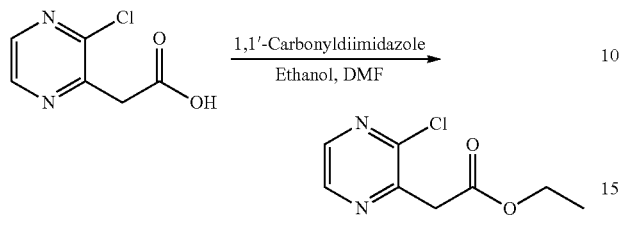

To a solution of (3-chloro-pyrazin-2-yl)-acetic acid (2.00 g) in N,N-dimethylformamide ("DMF") (20 ml) was added 1,1'-carbonyldiimidazole (1.88 g) and the mixture stirred for 1 hour. To the reaction mixture was added ethanol (20 ml) and the mixture stirred for 1 hour at ambient temperature. The reaction mixture was concentrated and then purified by chromatography on silica gel (eluent 5-95% ethyl acetate in isohexane) to give (3-chloro-pyrazin-2-yl)-acetic acid ethyl ester (1.93 g). 1H-NMR (400 MHz, CDCl$_3$): 8.50 (s, 1H), 8.30 (s, 1H), 4.20 (q, 2H), 4.00 (s, 2H), 1.30 (t, 3H) ppm.

Example 1.4

Preparation of 2-(3-Chloro-pyrazin-2-yl)-2-methyl-propionic acid ethyl ester

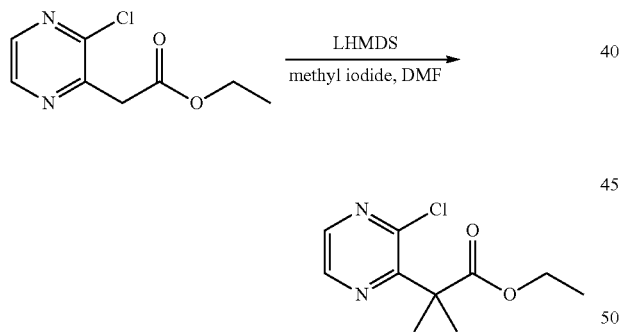

To a solution of (3-chloro-pyrazin-2-yl)-acetic acid ethyl ester (1.00 g) in N,N-dimethylformamide ("DMF") (10 ml) at 5-10° C. was added lithiumhexamethyldisilazide ("LHMDS", 1M in tetrahydrofuran) (7.47 ml) dropwise followed by methyl iodide (0.84 g) and the mixture stirred for 30 min at ambient temperature. The solution was cooled to 5-10° C. and a second portion of lithium hexamethyldisilazide ("LHMDS", 1M in tetrahydrofuran) (7.47 ml) added dropwise followed by a second portion of methyl iodide (0.84 g) and the mixture stirred for 120 min. The reaction was neutralised by the addition of 1M hydrochloric acid, diluted with water and extracted with dichloromethane (3×). The combined organic layers were dried (magnesium sulfate), filtered and the filtrate concentrated. The residue was purified by chromatography on silica gel (eluent 5-95% ethyl acetate in isohexane) to give 2-(3-Chloro-pyrazin-2-yl)-2-methyl-propionic acid ethyl ester (0.70 g). MH$^+$=229, RT=1.51 min (Method A).

Example 1.5

Preparation of 2-(3-Chloro-pyrazin-2-yl)-2-methyl-butyric acid methyl ester

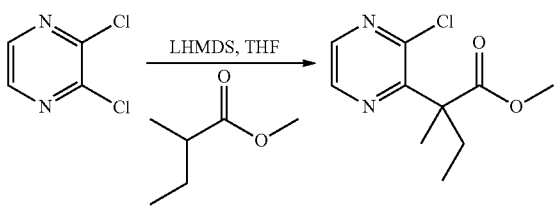

To a solution of 2,3-dichloro-pyrazine (0.50 g) (commercially available) and anhydrous tetrahydrofuran ("THF") (5 ml) was added a solution of lithium hexamethyldisilazide ("LHMDS", 1M in tetrahydrofuran) (5 ml). The reaction mixture was stirred for 16 hours. The reaction mixture was poured onto 1M hydrochloric acid and extracted with ethyl acetate (3×). The combined organic layers were dried (magnesium sulfate), filtered and the filtrate concentrated. The residue was purified by chromatography on silica gel (eluent 5-95% ethyl acetate in isohexane) to give 2-(3-Chloro-pyrazin-2-yl)-2-methyl-butyric acid methyl ester (compound A1 of Table A) (0.55 g). MH$^+$=229, RT=1.55 min (Method A).

Table (A) below shows characterising physical data for esters of formula (6) where R$^1$ and R$^2$ are hydrogen, R$^6$ is methyl and R$^{3a}$ and R$^{3b}$ have the values indicated.

(6)

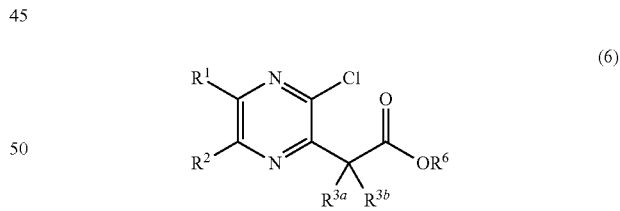

TABLE A

| Compound. | R$^{3a}$ | R$^{3b}$ | MH+ | RT (min) | LCMS Method |
|---|---|---|---|---|---|
| A1 | methyl | ethyl | 229 | 1.55 | A |
| A2 | methyl | allyl | 255 | 1.70 | A |
| A3 | methyl | phenyl | 277 | 1.65 | A |
| A4 | cyclopentyl | cyclopentyl | 241 | 1.60 | A |

Example 2

Reactions Covered by Reaction Scheme 2

Example 2.1

Preparation of 2-Methyl-2-(3-phenylethynyl-pyrazin-2-yl)-propionic acid ethyl ester

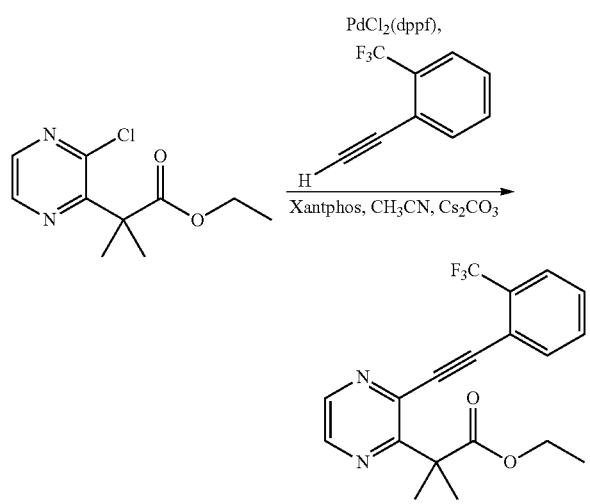

To a solution of 2-(3-Chloro-pyrazin-2-yl)-2-methyl-propionic acid ethyl ester (0.70 g) in acetonitrile (7.0 ml) was added 1-ethynyl-2-trifluoromethylbenzene (0.781 g) and caesium carbonate ("Cs$_2$CO$_3$") (2.99 g) and nitrogen bubbled through the solution for 20 min. To this solution was added as 4,5-(bisdiphenylphosphino)-9,9-dimethylxanthene ("Xantphos") (0.133 g) and (1,1'-bis(diphenylphosphino)-ferrocene)dichloro palladium(2) (0.125 g) and the reaction mixture heated to reflux for 30 min. The reaction mixture was cooled to ambient temperature then filtered and concentrated. The residue was purified by chromatography on silica gel (eluent 5-95% ethyl acetate in isohexane) to give 2-methyl-2-(3-phenylethynyl-pyrazin-2-yl)-propionic acid ethyl ester (compound B1 of Table B) (0.52 g).

Table (B) below shows characterising physical data for esters of formula (8) where $R^1$ and $R^2$ are hydrogen, $R^{3a}$ and $R^{3b}$ are methyl, $R^6$ are ethyl and $R^4$ have the values indicated.

(8)

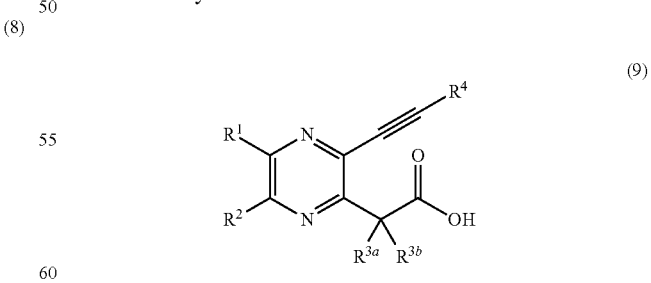

TABLE B

| Compound | $R^4$ | MH+ | RT (min) | LCMS Method |
|---|---|---|---|---|
| B1 | 2-Trifluoromethyl-phenyl- | 363 | 1.85 | A |
| B2 | 2-Methoxy-phenyl- | 325 | 1.68 | A |

TABLE B-continued

| Compound | $R^4$ | MH+ | RT (min) | LCMS Method |
|---|---|---|---|---|
| B3 | 2,4-Difluoro-phenyl- | 331 | 1.78 | A |
| B4 | 2-Chloro-phenyl- | 329 | 1.80 | A |
| B5 | 2-Methyl-phenyl- | 309 | 1.82 | A |
| B6 | 4-Chloro-phenyl- | 329 | 1.88 | A |
| B7 | 3-Trifluoromethyl-phenyl- | 363 | 1.92 | A |

Example 2.2

Preparation of 2-Methyl-2-[3-(2-trifluoromethyl-phenylethynyl)-pyrazin-2-yl]-propionic acid

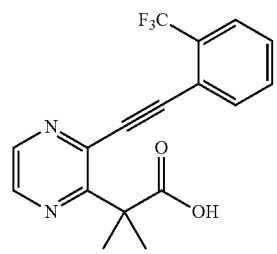

To a solution of 2-methyl-2-(3-phenylethynyl-pyrazin-2-yl)-propionic acid ethyl ester (0.52 g) in ethanol (5 ml) was added 4M sodium hydroxide (2.5 ml) and the reaction mixture heated to 80° C. for 8 hours. The reaction mixture was cooled to ambient temperature then poured onto water and 2M hydrochloric acid followed by extraction with ethyl acetate (3×). The combined organic layers were dried (magnesium sulfate), filtered and the filtrate concentrated to give 2-methyl-2-[3-(2-trifluoromethyl-phenylethynyl)-pyrazin-2-yl]-propionic acid (compound C1 of Table C) (0.48 g).

Table (C) below shows characterising physical data for esters of formula (9) where $R^1$ and $R^2$ are hydrogen, $R^{3a}$ and $R^{3b}$ are methyl and $R^4$ have the values indicated.

(9)

| Compound. | $R_4$ | MH+ | RT (min) | LCMS Method |
|---|---|---|---|---|
| C1 | 2-Trifluoromethyl-phenyl- | 335 | 1.50 | A |
| C2 | 2-Methoxy-phenyl- | 297 | 1.47 | A |

-continued

| Compound. | R4 | MH+ | RT (min) | LCMS Method |
|---|---|---|---|---|
| C3 | 2,4-Difluoro-phenyl- | 303 | 1.48 | A |
| C4 | 2-Chloro-phenyl- | 301 | 1.50 | A |
| C5 | 2-Methyl-phenyl- | 281 | 1.48 | A |
| C6 | 4-Chloro-phenyl- | 301 | 1.55 | A |
| C7 | 3-Trifluoromethyl-phenyl- | 335 | 1.62 | A |

Example 2.3

Preparation of 8,8-Dimethyl-5-[1-(2-trifluoromethyl-phenyl)-meth-(Z)-ylidene]-5,8-dihydro-pyrano[3,4-b]pyrazin-7-one

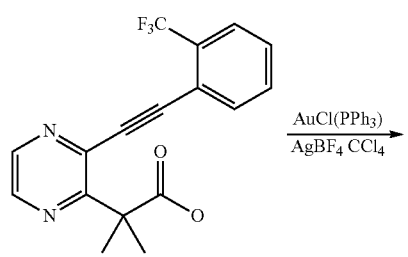

A solution of gold chloride triphenylphosphine (0.444 g) and silver tetrafluoroborate (0.174 g) in carbon tetrachloride was stirred for 30 min. To this solution was added a solution of 2-methyl-2-[3-(2-trifluoromethyl-phenylethynyl)-pyrazin-2-yl]-propionic acid (0.50 g). The reaction mixture was flushed out with argon then heated to 55° C. for 48 hours. The reaction mixture was cooled to ambient temperature, filtered, concentrated and the residue purified by chromatography on silica gel (eluent 5-95% ethyl acetate in isohexane) to give 8,8-dimethyl-5-[1-(2-trifluoromethyl-phenyl)-meth-(Z)-ylidene]-5,8-dihydro-pyrano[3,4-b]pyrazin-7-one (compound D1 of Table D) (0.170 g).

Table (D) below shows physical characterising data for esters of formula (10), in which $R^1$ and $R^2$ are both hydrogen, $R^{3a}$ and $R^{3b}$ are both methyl, and $R^4$ has the value indicated.

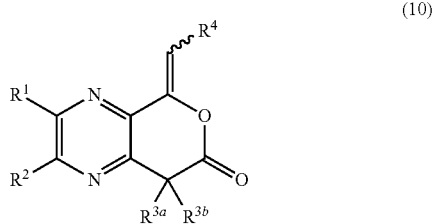

(10)

| Compound | $R^4$ | MH+ | RT (min) | LCMS Method | 1H-NMR (400 MHz, chemical shifts in ppm) |
|---|---|---|---|---|---|
| D1 | 2-Trifluoromethyl-phenyl- | — | — | — | 8.60 (s, 2H), 8.20 (d, 1H), 7.70 (d, 1H), 7.60 (t, 1H), 7.50 (s, 1H), 7.40 (t, 1H), 1.70 (s, 6H) CDCl3 |
| D2 | 2-Methoxy-phenyl- | 297 | 1.77 | A | |
| D3 | 2,4-Difluoro-phenyl- | 303 | 1.82 | A | |
| D4 | 2-Chloro-phenyl- | 301 | 1.85 | A | |
| D5 | 2-Methyl-phenyl- | 281 | 1.78 | A | |
| D6 | 4-Chloro-phenyl- | 301 | 1.87 | A | |
| D7 | 3-Trifluoromethyl-phenyl- | 335 | 1.90 | A | |

Example 2.4

Preparation of 8,8-Dimethyl-6-(2-trifluoromethyl-phenyl)-8H-quinoxaline-5,7-dione

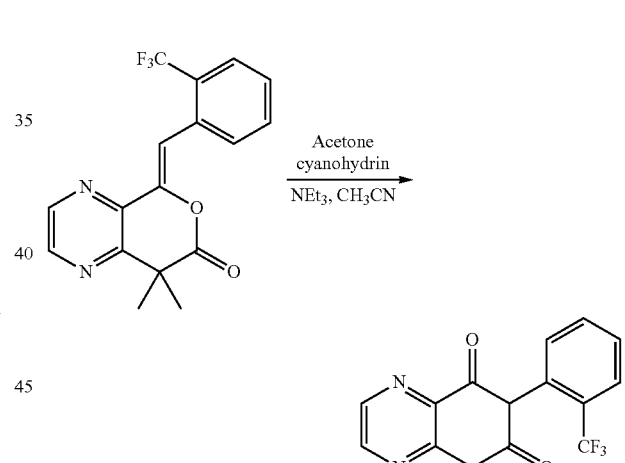

To a stirred solution of 8,8-dimethyl-5-[1-(2-trifluoromethyl-phenyl)-meth-(Z)-ylidene]-5,8-dihydro-pyrano[3,4-b]pyrazin-7-one (0.170 g) in acetonitrile (1.7 ml) at ambient temperature was added triethylamine (0.154 g) and 4□ molecular sieves. After 10 min acetone cyanohydrin (0.013 g) was added and the reaction mixture stirred for 16 hours. The reaction mixture was concentrated and the residue purified by chromatography on silica gel (eluent 5-95% ethyl acetate in isohexane) to give the crude 8,8-dimethyl-6-(2-trifluoromethyl-phenyl)-8H-quinoxaline-5,7-dione (compound E1 of Table E) (0.190 g) which was carried over to the next step.

Table (E) shows characterising physical data for compounds of formula (11a) wherein $R^4$ has the value indicated, and which can be prepared in a similar manner to Example 2.4 described immediately above.

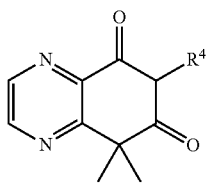

(11a)

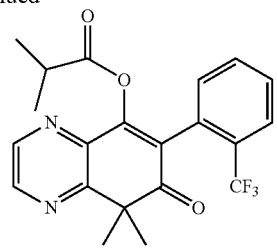

| Compound | R⁴ | MH+ | RT (min) | LCMS Method |
|---|---|---|---|---|
| E1 | 2-trifluoromethyl-phenyl- | 335 | 1.47 | A |
| E2 | 2-methoxy-phenyl- | 297 | 1.47 | A |
| E3 | 2,4-difluoro-phenyl- | 303 | 1.47 | A |
| E4 | 2-chloro-phenyl- | 301 | 1.47 | A |
| E5 | 2-methyl-phenyl- | 281 | 1.45 | A |
| E6 | 4-chloro-phenyl- | 301 | 1.58 | A |
| E7 | 3-trifluoromethyl-phenyl- | 335 | 1.64 | A |

Example 2.5

Preparation of Isobutyric acid 8,8-dimethyl-7-oxo-6-(2-trifluoromethyl-phenyl)-7,8-dihydro-quinoxalin-5-yl ester

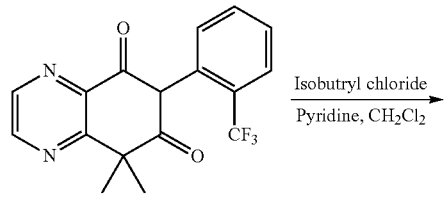

To a stirred solution of crude 8,8-dimethyl-6-(2-trifluoromethyl-phenyl)-8H-quinoxaline-5,7-dione (0.190 g) in dichloromethane (2.0 ml) at ambient temperature was added pyridine (0.054 g) followed by isobutryl chloride (isopropyl-C(O)—Cl, 0.064 g) and the reaction mixture stirred for 1 hour. The reaction mixture was concentrated and the residue purified by chromatography on silica gel (eluent 5-95% ethyl acetate in isohexane) to give isobutyric acid 8,8-dimethyl-7-oxo-6-(2-trifluoromethyl-phenyl)-7,8-dihydro-quinoxalin-5-yl ester (compound F1 of Table F) (0.162 g).

Table (F) shows characterising physical data for ester compounds of formula (12a) wherein R⁴ has the value indicated, and which can be prepared in a similar manner to Example 2.5 immediately above.

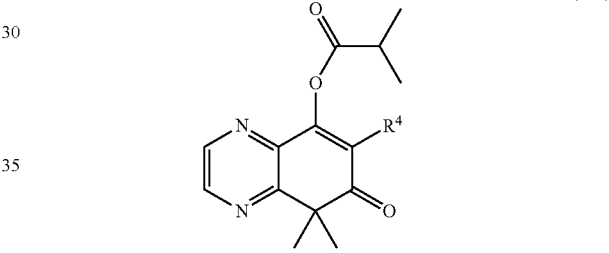

(12a)

| Compound | R⁴ | MH+ | RT (min) | LCMS Method | ¹H-NMR (400 MHz, chemical shifts in ppm) |
|---|---|---|---|---|---|
| F1 | 2-trifluoromethyl-phenyl- | — | — | — | 8.60 (s, 1H), 8.50 (s, 1H), 7.75 (d, 1H), 7.60 (t, 1H), 7.50 (t, 1H), 7.20 (d, 1H), 2.70 (m, 1H), 1.70 (s, 3H), 1.60 (s, 3H), 1.05 (d, 3H), 0.95 (d, 3H) CDCl₃ |
| F2 | 2,4-difluoro-phenyl- | 373 | 1.87 | A | 8.60 (s, 1H), 8.50 (s, 1H), 7.25 (d, 1H), 6.90 (m, 2H), 2.80 (m, 1H), 1.65 (s, 6H), 1.20 (d, 6H) CDCl₃ |
| F3 | 2-chloro-phenyl- | 371 | 1.87 | A | 8.60 (s, 1H), 8.50 (s, 1H), 7.50 (d, 1H), 7.20-7.40 (m, 3H), 2.75 (m, 1H), 1.70 (s, 3H), 1.65 (s, 3H), 1.15 (d, 3H), 1.10 (d, 3H) CDCl₃ |
| F4 | 2-methyl-phenyl- | 351 | 1.88 | A | 8.60 (s, 1H), 8.50 (s, 1H), 7.20-7.30 (m, 3H), 7.10 (d, 1H), 2.70 (m, 1H), 2.15 (s, 3H), 1.70 (s, 3H), 1.65 (s, 3H), 1.00 (d, 6H) CDCl₃ |
| F5 | 4-chloro-phenyl- | 371 | 1.95 | A | |
| F6 | 3-trifluoromethyl-phenyl- | 405 | 1.98 | A | |

Example 2.6

Preparation of 8,8-Dimethyl-6-(2-trifluoromethyl-phenyl)-8H-quinoxaline-5,7-dione

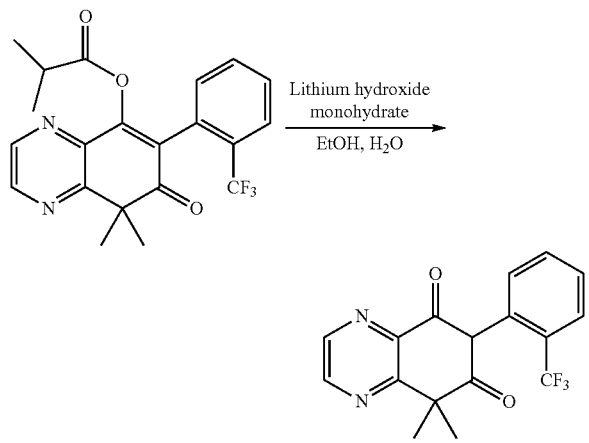

To a solution of 8,8-dimethyl-6-(2-trifluoromethyl-phenyl)-8H-quinoxaline-5,7-dione (0.121 g) in ethanol (0.60 ml) was added water (0.60 ml) and lithium hydroxide monohydrate (0.025 g), and the reaction mixture stirred for 2 hours at ambient temperature. The reaction mixture was reduced then quenched with 1M hydrochloric acid followed by extraction with chloroform (3×). The combined organic layers were dried (magnesium sulfate), filtered and the filtrate concentrated. The residue was slurried in diethyl ether to give 8,8-dimethyl-6-(2-trifluoromethyl-phenyl)-8H-quinoxaline-5,7-dione (compound E1 of Table E) (0.030 g). 1H-NMR (400 MHz, CDCl$_3$): 8.75 (s, 1H), 8.50 (s, 1H), 7.80 (d, 1H), 7.60 (t, 1H), 7.50 (t, 1H), 7.30 (d, 1H), 1.65 (s, 3H), 1.60 (s, 3H) ppm.
LCMS analysis: Method A
Note: Compounds characterised by HPLC-MS were analysed using an Agilent 1100 Series HPLC equipped with a Waters Atlantis dC18 column (column length 20 mm, internal diameter of column 3 mm, particle size 3 micron, temperature 40° C.), Waters photodiode array and Micromass ZQ2000. The analysis was conducted using a three minute run time, according to the gradient table shown below.

| Gradient Table | | | |
|---|---|---|---|
| Time (mins) | Solvent A (%) | Solvent B (%) | Flow (ml/mn) |
| 0.00 | 90.0 | 10.0 | 2.00 |
| 0.25 | 90.0 | 10.0 | 2.00 |
| 2.00 | 10.0 | 90.0 | 2.00 |
| 2.50 | 10.0 | 90.0 | 2.00 |
| 2.6 | 90.0 | 10.0 | 2.00 |
| 3.0 | 90.0 | 10.0 | 2.00 |

Solvent A: H$_2$O with 0.1% HCOOH
Solvent B: 0.1% HCOOH in CH$_3$CN

Biological Examples

Example B1

Herbicidal Action Post-Emergence

Seeds of a variety of test species were sown in standard soil in pots. After 8 days cultivation (post-emergence) under controlled conditions in a glasshouse (at 24/16° C., day/night; 14 hours light; 65% humidity), the plants were sprayed with an aqueous spray solution derived from the formulation of the technical active ingredient in acetone/water (50:50) solution containing 0.5% Tween 20 (polyoxyethelyene sorbitan monolaurate, CAS RN 9005-64-5). The test plants were then grown under controlled conditions in a glasshouse (at 24/16° C., day/night; 14 hours light; 65% humidity) and watered twice daily. After 13 days, the test was evaluated (10=total damage to plant; 0=no damage to plant).

TABLE B1

| | | Application post-emergence | | | | |
|---|---|---|---|---|---|---|
| Compound | Rate (g/ha) | SOLNI | AMARE | SETFA | ECHCG | IPOHE |
| E1 | 1000 | 10 | 10 | 9 | 9 | 9 |

SOLNI = *Solanum nigrum*; AMARE = *Amaranthus retroflexus*; SETFA = *Setaria faberi*; ECHCG = *Echinochloa crus-galli*; IPOHE = *Ipomea hederaceae*.

Example B2

Herbicidal Action Post-Emergence

Seeds of crop and representative weed species were sown in standard soil in pots. After cultivation for 14 days under controlled conditions in a glasshouse (at 22/16° C., day/night; 16 hours light; 65% humidity), the plants were sprayed. The spray solution was prepared by dissolving the technical active ingredient in acetone containing 10.56 wt % Emulsogen EL, 42.22 wt % N-methylpyrrolidone and 2.22 wt % DPG-monoethyl ether to give a 5% stock solution. This was then diluted with water containing 0.2% (v/v) of the adjuvant X-77 to give the desired treatment concentration.
The test plants were then grown on under controlled conditions in a glasshouse (at 22/16° C., day/night; 16 hours light; 65% humidity) and watered twice daily. After 15 days the test was evaluated (10=total damage to plant; 0=no damage to plant). Results are shown below in Table B2.

TABLE B2

| | Application post-emergence | | | |
|---|---|---|---|---|
| Compound | Rate (g/ha) | AMARE | SETFA | ECHCG | IPOHE |
| E1 | 500 | 10 | 7 | 3 | 8 |
| F1 | 500 | 10 | 8 | 8 | 8 |

AMARE = *Amaranthus retroflexus*; SETFA = *Setaria faberi*; ECHCG = *Echinochloa crus-galli*; IPOHE = *Ipomea hederaceae*.

The invention claimed is:
1. A compound of formula (I):

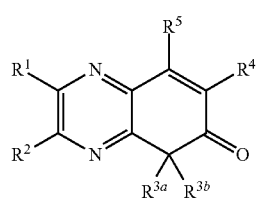

wherein:
$R^1$ and $R^2$ are independently hydrogen, halogen, $C_1$-$C_4$alkyl, $C_1$-$C_2$fluoroalkyl, $C_1$-$C_2$alkoxy-$C_1$-

$C_2$alkyl-, hydroxy, $C_1$-$C_4$alkoxy, $C_1$-$C_2$fluoroalkoxy, or $C_1$-$C_2$alkoxy-$CH_2CH_2O$—;

$R^{3a}$ and $R^{3b}$ are independently halogen, $C_1$-$C_4$alkyl, $C_1$-$C_4$fluoroalkyl, $C_1$-$C_4$chloroalkyl, $C_1$-$C_2$alkoxy-$C_1$-$C_2$alkyl-, $C_2$-$C_4$alkenyl, $C_2$-$C_4$fluoroalkenyl, $C_2$-$C_4$chloroalkenyl, $C_2$-$C_4$alkynyl, $C_2$-$C_4$fluoroalkynyl, $C_2$-$C_4$chloroalkynyl, $C_3$-$C_6$cycloalkyl-$(CH_2)_m$- or $C_3$-$C_6$cycloalkyl-$(CH_2)_m$- substituted on the cycloalkyl ring by 1 or 2 methyl groups and wherein m is 0 or 1, $C_1$-$C_3$alkyl-carbonyl-, $C_1$-$C_3$alkoxy-carbonyl-, $C_1$-$C_2$chloroalkyl-carbonyl-, or $C_1$-$C_2$fluoroalkyl-carbonyl-; phenyl or phenyl substituted by one or two substituents independently selected from fluorine and methyl; or heterocyclyl-methyl- in which the heterocyclyl is a 4-, 5-, or 6-membered saturated monocyclic heterocyclic ring in which there are 1 or 2 ring heteroatoms independently selected from O, N and S and wherein the heterocyclyl is optionally substituted on a ring carbon and/or (if present) on a ring nitrogen by 1 or 2 methyl groups; or heteroaryl-methyl- in which the heteroaryl is a 5-membered monocyclic heteroaromatic ring in which there are 1, 2 or 3 ring heteroatoms independently selected from O, N and S and wherein the heteroaryl is optionally substituted on the ring by 1 or 2 methyl groups;

$R^4$ is of sub-formula (a) or sub-formula (b):

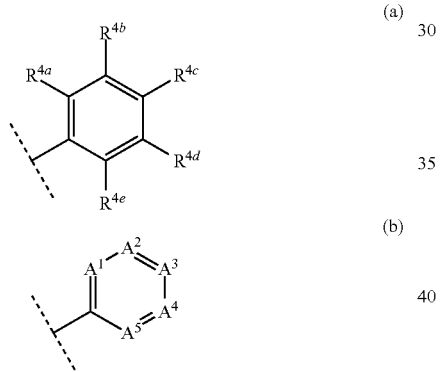

wherein, in sub-formula (a):

$R^{4a}$ and $R^{4e}$ are independently hydrogen, halogen, $C_1$-$C_2$alkyl, $C_1$fluoroalkyl, hydroxy, $C_1$-$C_2$alkoxy, $C_1$fluoroalkoxy, $H_3C$—$S(O)_2$—, $H_2N$—$S(O)_2$—, $H_3CNH$—$S(O)_2$—, or $(H_3C)_2N$—$S(O)_2$—; and $R^{4b}$, $R^{4c}$ and $R^{4d}$ are independently hydrogen, halogen, cyano, $C_1$-$C_4$alkyl, $C_1$-$C_2$fluoroalkyl, $C_1$-$C_3$alkoxy-$C_1$-$C_2$alkyl-, $C_1$fluoroalkoxy-$C_1$-$C_2$alkyl-, $H_3COCH_2CH_2OCH_2$—, $C_3$-$C_6$cycloalkyl, hydroxy, $C_1$-$C_4$alkoxy, $C_1$-$C_2$fluoroalkoxy, HS—, $C_1$-$C_3$alkylthio-, $C_1$ fluoroalkylthio-, $C_1$-$C_3$alkyl-$S(O)$—, $C_1$fluoroalkyl-$S(O)$—, $C_1$-$C_3$alkyl-$S(O)_2$$C_1$fluoroalkyl-$S(O)_2$, $H_2N$—$S(O)_2$—, $C_1$-$C_4$alkyl-NH—$S(O)_2$—, $(C_1$-$C_3$alkyl$)_2$N—$S(O)_2$—, $C_1$-$C_4$alkyl-C(O)—, H—C(O)—, $C_1$-$C_3$alkoxy-C(O)—, HO—C(O)—, $H_2N$—C(O)—, $C_1$-$C_4$alkyl-NH—C(O)—, $(C_1$-$C_3$alkyl$)_2$N—C(O)—, (1-pyrrolidinyl)-C(O)—(1-piperidinyl)-C(O)—, amino, $C_1$-$C_4$alkyl-NH—, $(C_1$-$C_3$alkyl$)_2$N—, 1-pyrrolidinyl, 1-piperidinyl, $C_1$-$C_4$alkyl-C(O)—NH—, H—C(O)—NH—, $C_1$-$C_3$alkyl-C(O)—N($C_1$-$C_3$alkyl)-, 2-oxo-1-pyrrolidinyl, 2-oxo-1-piperidinyl, $C_1$-$C_3$alkyl-$S(O)_2$—NH—, $C_1$-$C_3$alkyl-$S(O)_2$—N($C_1$-$C_3$alkyl)-, phenyl or phenyl substituted by one, two or three of $R^7$, or phenoxy or phenoxy substituted by one, two or three of $R^7$;

provided that none of, or only one of, $R^{4b}$, $R^{4c}$ and $R^{4d}$ is $C_3$-$C_6$cycloalkyl, (1-pyrrolidinyl)-C(O)—, (1-piperidinyl)-C(O)—, 1-pyrrolidinyl, 1-piperidinyl, 2-oxo-1pyrrolidinyl, 2-oxo-1piperidinyl, phenyl, substituted phenyl, phenoxy or substituted phenoxy;

wherein each $R^7$ is independently fluoro, chloro, $C_1$-$C_2$alkyl, $C_1$fluoroalkyl, $C_1$-$C_2$alkoxy or $C_1$fluoroalkoxy;

and wherein, in sub-formula (b):

$A^1$ is N or C—$R^{4f}$, $A^2$ is N or C—$R^{4g}$, $A^3$ is N or C—$R^{4h}$, $A^4$ is N or C—$R^{4i}$, and $A^5$ is N or C—$R^{4j}$, provided that one or two of $A^1$, $A^2$, $A^3$, $A^4$ and $A^5$ are nitrogen and the remaining ones of $A^1$, $A^2$, $A^3$, $A^4$ and $A^5$ are not nitrogen;

wherein $R^{4f}$ and $R^{4j}$ are independently hydrogen, halogen, $C_1$-$C_2$alkyl, $C_1$fluoroalkyl, hydroxy or a tautomer thereof $C_1$-$C_2$alkoxy, or $C_1$fluoroalkoxy; and $R^{4g}$, $R^{4h}$ and $R^{4i}$ are independently hydrogen, halogen, $C_1$-$C_4$alkyl, $C_1$-$C_2$fluoroalkyl, $C_1$-$C_3$alkoxy-$CH_2$—, $C_1$fluoroalkoxy-$CH_2$—, $H_3COCH_2CH_2OCH_2$—, $C_3$-$C_6$cycloalkyl, hydroxy or a tautomer thereof, $C_1$-$C_4$alkoxy, $C_1$-$C_2$fluoroalkoxy, $C_1$-$C_4$alkyl-C(O)—, H—C(O)—, $C_1$-$C_3$alkoxy-C(O)—, HO—C(O)—, $H_2N$—C(O)—, $C_1$-$C_4$alkyl-NH—C(O)—, $(C_1$-$C_3$alkyl$)_2$N—C(O)—, (1-pyrrolidinyl)-C(O)—, (1-piperidinyl)-C(O)—, amino, $C_1$-$C_4$alkyl-NH—, $(C_1$-$C_3$alkyl$)_2$N—, 1-pyrrolidinyl, 1-piperidinyl, $C_1$-$C_4$alkyl-C(O)—NH—, H—C(O)—NH—, $C_1$-$C_3$alkyl-C(O)—N($C_1$-$C_3$alkyl)-, 2-oxo-1pyrrolidinyl, 2-oxo-1-piperidinyl, phenyl or phenyl substituted by one, two or three of $R^7$, or phenoxy or phenoxy substituted by one, two or three of $R^7$; wherein $R^7$ is as defined hereinabove;

provided that none of, or only one of, $R^{4g}$, $R^{4h}$ and $R^{4i}$ is $C_3$-$C_6$cycloalkyl, (1-pyrrolidinyl)-C(O)—, (1-piperidinyl)-C(O)—, 1-pyrrolidinyl, 1-piperidinyl, 2-oxo-1pyrrolidinyl, 2-oxo-1piperidinyl, phenyl, substituted phenyl, phenoxy or substituted phenoxy; and $R^5$ is hydroxy, $R^6$-oxy-, $R^8$—C(O)—O—, $C_1$-$C_{10}$alkyl-$S(O)_2O$—, $C_1$fluoroalkyl-$S(O)_2O$—, $C_1$chloroalkyl-$S(O)_2O$—, phenyl-$S(O)_2O$— or (4-methyl-phenyl)-$S(O)_2O$—;

wherein $R^6$ is $C_1$-$C_{10}$alkyl, $C_1$-$C_4$fluoroalkyl, $C_2$-$C_{10}$alkenyl, $C_2$-$C_{10}$alkynyl, $C_3$-$C_8$cycloalkyl, $C_3$-$C_8$cycloalkyl-$C_1$-$C_4$alkyl-, $C_1$-$C_4$alkoxy-$CH_2CH_2$—, $C_1$-$C_4$alkoxy-$CH_2CH_2CH_2$—, phenyl-$C_1$-$C_4$alkyl-, or phenyl-$C_1$-$C_4$alkyl- wherein the phenyl moiety is substituted by one, two or three $R^9$;

$R^8$ is $C_1$-$C_{10}$alkyl, $C_1$-$C_4$fluoroalkyl, $C_2$-$C_{10}$alkenyl, $C_2$-$C_{10}$alkynyl, $C_3$-$C_8$cycloalkyl, $C_3$-$C_8$cycloalkyl-$C_1$-$C_4$alkyl-, $C_1$-$C_4$alkoxy-$C_1$-$C_4$alkyl-, phenyl, phenyl substituted by one, two or three $R^9$, phenyl-$C_1$-$C_4$alkyl-, or phenyl-$C_1$-$C_4$alkyl- wherein the phenyl moiety is substituted by one, two or three $R^9$;

or $R^8$ is $C_1$-$C_{10}$alkoxy, $C_1$-$C_4$fluoroalkoxy, $C_1$-$C_{10}$alkenyloxy, $C_1$-$C_{10}$alkynyloxy, $C_3$-$C_8$cycloalkoxy, $C_3$-$C_8$cycloalkyl-$C_1$-$C_4$alkoxy-, $C_1$-$C_4$alkoxy-$CH_2CH_2O$—, $C_1$-$C_4$alkoxy-$CH_2CH_2CH_2O$—, phenoxy, phenoxy substituted by one, two or three $R^9$, phenyl-$C_1$-$C_4$alkoxy-, or phenyl-$C_1$-$C_4$alkoxy- wherein the phenyl moiety is substituted by one, two or three $R^9$;

or $R^8$ is $C_1$-$C_{10}$alkylthio-, $C_1$-$C_{10}$alkyl-NH—, or $(C_1$-$C_6$alkyl$)_2$N—;

and wherein each $R^9$ is independently fluoro, chloro, $C_1$-$C_4$alkyl, $C_1$fluoroalkyl, $C_1$-$C_3$alkoxy or $C_1$fluoroalkoxy;
or a salt thereof 2. The compound of formula (I) according to claim 1, wherein $R^4$ is an optionally substituted pyridinyl.

3. The compound of formula (I) according to claim 2, wherein $R^{4f}$ and $R^{4j}$ are independently hydrogen, fluoro, chloro, methyl, $C_1$fluoroalkyl, or hydroxy;
$R^{4g}$, $R^{4h}$ and $R^{4i}$ are independently hydrogen, fluoro, chloro, $C_1$-$C_4$alkyl, $C_1$fluoroalkyl, $H_3COCH_2$—, $H_3COCH_2CH_2OCH_2$—, $C_3$-$C_5$cycloalkyl, hydroxy, $C_1$-$C_3$alkoxy, $C_1$fluoroalkoxy, phenyl or phenyl substituted by one, two or three of $R^7$;
and wherein each $R^7$ is independently fluoro, chloro, methyl, $C_1$fluoroalkyl, $C_1$alkoxy or $C_1$fluoroalkoxy, provided that none of, or only one of, $R^{4g}$, $R^{4h}$ and $R^{4i}$ is $C_3$-$C_5$cycloalkyl, phenyl or substituted phenyl.

4. The compound of formula (I) according to claim 1, wherein $R^1$ and $R^2$ are each independently hydrogen, halogen, $C_1$-$C_3$alkyl, $C_1$fluoroalkyl, $C_1$-$C_2$alkoxy, or $C_1$fluoroalkoxy.

5. The compound of formula (I) according to claim 1 wherein $R^1$ and $R^2$ are each independently hydrogen, fluoro, chloro, methyl or ethyl.

6. The compound of formula (I) according to claim 1, wherein $R^{3a}$ and $R^{3b}$ are each independently $C_1$-$C_4$alkyl, $C_1$-$C_3$fluoroalkyl, $C_2$-$C_3$alkenyl, $C_2$-$C_3$fluoroalkenyl, $C_2$chloroalkenyl, $C_2$-$C_3$alkynyl, $C_3$-$C_5$cycloalkyl, $C_3$-$C_4$cycloalkyl-$CH_2$—, or phenyl.

7. The compound of formula (I) according to claim 1, wherein $R^{3a}$ and $R^{3b}$ are each independently methyl, ethyl, n-propyl, isopropyl, $C_2$fluoroalkyl, vinyl, allyl, $C_2$fluoroalkenyl, propargyl, cyclopropyl, cyclobutyl, cyclopentyl, cyclopropyl-$CH_2$, or phenyl.

8. The compound of formula (I) according to claim 1, whererin $R^4$ is of sub-formula (a) and,
$R^{4a}$ and $R^{4e}$ are independently hydrogen, fluoro, chloro, bromo, methyl, $C_1$fluoroalkyl, $C_1$alkoxy, $C_1$fluoroalkoxy or $H_3C$—$S(O)_2$—;
$R^{4b}$, $R^{4c}$ and $R^{4d}$ are independently hydrogen, halogen, $C_1$-$C_4$alkyl, $C_1$fluoroalkyl, $H_3COCH_2$—, $H_3COCH_2CH_2OCH_2$—, $C_3$-$C_5$cycloalkyl, $C_1$-$C_3$alkoxy, $C_1$fluoroalkoxy, $C_1$-$C_3$alkyl-$S(O)_2$—, $H_2N$—$S(O)_2$—, $C_1$-$C_3$alkyl-NH—$S(O)_2$—, or $(C_1$-$C_3$alkyl$)_2$N—$S(O)_2$—; phenyl or phenyl substituted by one or two of $R^7$;
and wherein each $R^7$ independently is fluoro, chloro, methyl, $C_1$fluoroalkyl, $C_1$alkoxy, or $C_1$fluoroalkoxy; provided that none of, or only one of, $R^{4b}$, $R^{4c}$ and $R^{4d}$ is $C_3$-$C_5$cycloalkyl, phenyl or substituted phenyl.

9. The compound of formula (I) according to claim 1, wherein $R^4$ is of sub-formula (a), and,
$R^{4a}$ and $R^{4e}$ are independently hydrogen, fluoro, chloro, bromo, methyl, $CF_3$ or $C_1$alkoxy;
$R^{4b}$, $R^{4c}$ and $R^{4d}$ are independently hydrogen, fluoro, chloro, bromo, methyl, ethyl, $C_1$fluoroalkyl, cyclopropyl, $C_1$alkoxy, $H_3CH_2CO$—, $C_1$fluoroalkoxy, $H_3C$—$S(O)_2$—, phenyl, or phenyl substituted by one or two of $R^7$;
and wherein each $R^7$, independently of any other $R^7$, is fluoro, chloro, methyl, $CF_3$, $C_1$alkoxy, $OCHF_2$ or $OCH_2F$;
provided that none of, or only one of, $R^{4b}$, $R^{4c}$ and $R^{4d}$ is cyclopropyl, phenyl or substituted phenyl.

10. The compound of formula (I) according to claim 1, wherein $R^5$ is hydroxy, $R^6$-oxy- or $R^8$—C(O)—O—.

11. The compound of formula (I) according to claim 1, wherein $R^5$ is hydroxy or $R^8$—C(O)—O—.

12. A herbicidal composition which comprises a herbicidally effective amount of a compound of formula (I) as defined in claim 1 in addition to at least one formulation carrier, and/or solvent.

13. A method of controlling unwanted plants which comprises applying to the plants or to the locus thereof a herbicidally effective amount of a compound of formula (I) as defined in claim 1.

* * * * *